US011045095B2

(12) United States Patent
Tao et al.

(10) Patent No.: US 11,045,095 B2
(45) Date of Patent: Jun. 29, 2021

(54) SYSTEMS AND METHODS FOR NON-CONTACT MONITORING OF BALLISTOCARDIOGRAM, PHOTOPLETHYSMOGRAM, BLOOD PRESSURE AND ABNORMAL HEART RHYTHM

(71) Applicants: ARIZONA BOARD OF REGENTS ON BEHALF OF ARIZONA STATE UNIVERSITY, Tempe, AZ (US); Nongjian Tao, Fountain Hills, AZ (US); Dangdang Shao, Tempe, AZ (US)

(72) Inventors: Nongjian Tao, Tempe, AZ (US); Dangdang Shao, Tempe, AZ (US)

(73) Assignee: Arizona Board of Regents on Behalf of Arizona State University, Tempe, AZ (US)

(*) Notice: Subject to any disclaimer, the term of this patent is extended or adjusted under 35 U.S.C. 154(b) by 38 days.

(21) Appl. No.: 16/083,052

(22) PCT Filed: Mar. 8, 2017

(86) PCT No.: PCT/US2017/021302
§ 371 (c)(1),
(2) Date: Sep. 7, 2018

(87) PCT Pub. No.: WO2017/156084
PCT Pub. Date: Sep. 14, 2017

(65) Prior Publication Data
US 2019/0082972 A1 Mar. 21, 2019

Related U.S. Application Data

(60) Provisional application No. 62/307,064, filed on Mar. 11, 2016.

(51) Int. Cl.
G06K 9/00 (2006.01)
A61B 5/0205 (2006.01)
(Continued)

(52) U.S. Cl.
CPC .......... A61B 5/0205 (2013.01); A61B 5/0077 (2013.01); A61B 5/02125 (2013.01);
(Continued)

(58) Field of Classification Search
CPC . A61B 5/0205; A61B 5/0077; A61B 5/02125; A61B 5/02416; A61B 5/1102; G06T 7/20; G06T 2207/30076
(Continued)

(56) References Cited

U.S. PATENT DOCUMENTS 10,078,074 B2    9/2018  Tsow et al.
10,078,795 B2    9/2018  Tao et al.
(Continued)

FOREIGN PATENT DOCUMENTS

WO    2013019843 A2    2/2013
WO    2014116604 A1    7/2014
(Continued)

OTHER PUBLICATIONS

Won, et al., "A touchscreen as a biomolecule detection platform," Angewandte Chemie, vol. 124, pp. 772-775, 2012.
(Continued)

Primary Examiner — Van D Huynh
(74) Attorney, Agent, or Firm — Polsinelli PC

(57) ABSTRACT

Various embodiments of systems and methods for tracking ballistocardiogram, photoplethysmogram, blood pressure and abnormal heart rhythm based on optical imaging of a human body are disclosed. Ballistocardiogram and photoplethysmogram signals from a similar region of the human body are simultaneously obtained, and the time delay
(Continued)

between the two signals is used to determine the blood pressure of the subject, together with other physiological parameters of the subject, including gender, age, weight, height, heart rate, stroke volume, blood pressure and abnormal heart rhythm obtained using other methods.

11 Claims, 28 Drawing Sheets

(51) Int. Cl.
    *A61B 5/00*     (2006.01)
    *A61B 5/021*     (2006.01)
    *A61B 5/024*     (2006.01)
    *A61B 5/11*     (2006.01)
    *G06T 7/20*     (2017.01)

(52) U.S. Cl.
    CPC ........ *A61B 5/02416* (2013.01); *A61B 5/1102* (2013.01); *G06T 7/20* (2013.01); *G06T 2207/30076* (2013.01)

(58) Field of Classification Search
    USPC .......................................................... 382/128
    See application file for complete search history.

(56) References Cited

U.S. PATENT DOCUMENTS

| | | | |
|---|---|---|---|
| 10,143,401 B2 | 12/2018 | Tao et al. | |
| 10,413,226 B2 | 9/2019 | Tao et al. | |
| 2007/0160286 A1 | 7/2007 | Haque | |
| 2009/0147991 A1 | 11/2009 | Chau | |
| 2013/0310700 A1* | 11/2013 | Wiard | A61B 5/742 600/485 |
| 2014/0043457 A1 | 2/2014 | Stergiou | |
| 2014/0142437 A1* | 5/2014 | Inan | A61B 5/1102 600/479 |
| 2014/0275833 A1 | 9/2014 | Vanderpohl | |
| 2014/0276104 A1 | 9/2014 | Tao et al. | |
| 2015/0005646 A1* | 1/2015 | Balakrishnan | A61B 5/0255 600/479 |
| 2015/0018637 A1 | 1/2015 | Chen | |
| 2015/0119737 A1* | 4/2015 | Brodnick | A61B 5/316 600/512 |
| 2016/0081566 A1* | 3/2016 | Xu | A61B 5/1102 600/450 |
| 2016/0106378 A1* | 4/2016 | Kyal | A61B 5/02416 600/408 |
| 2017/0238847 A1* | 8/2017 | Inan | A61B 5/6823 |
| 2018/0140255 A1 | 5/2018 | Tao et al. | |
| 2019/0029543 A1* | 1/2019 | Hutchinson | A61B 5/7485 |
| 2019/0094146 A1 | 3/2019 | Tao et al. | |
| 2019/0239761 A1 | 8/2019 | Tao et al. | |
| 2019/0325257 A1 | 10/2019 | Tao et al. | |

FOREIGN PATENT DOCUMENTS

| | | | |
|---|---|---|---|
| WO | 2018057753 A1 | 3/2018 | |
| WO | 2018170009 A1 | 9/2018 | |
| WO | 2019136097 A1 | 7/2019 | |

OTHER PUBLICATIONS

Wong, et al., "The relationship between pulse transit time and systolic blood pressure on individual subjects after exercises," 1st Transdisciplinary Conference on Distributed Diagnosis and Home Healthcare, 2006. D2H2., 2006, pp. 37-38.
Yu, et al., "A wireless physiological signal monitoring system with integrated bluetooth and WiFi technologies," Engineering in Medicine and Biology Society, 2005. IEEE-EMBS 2005. 27th Annual International Conference, 2006, pp. 2203-2206.
Zhao, et al., "Remote measurements of heart and respiration rates for telemedicine," PloS one, vol. 8, p. e71384, 2013.
Zonios, et al., "Pulse oximetry theory and calibration for low saturations," Biomedical Engineering, IEEE Transactions, vol. 51, pp. 818-822, 2004.
International Search Report and Written Opinion in corresponding Application No. PCT/US2017/021302 dated Jul. 25, 2017, 10 pages.
Moco et al., "Ballistocardiographic Artifacts in PPG Imaging" in IEEE Transactions on Biomedical Engineering, vol. 63, Issue 9, pp. 1804-1811, date of ePub: Nov. 20, 2015, 8 pages.
Mishra et al., "Heart Rate Measurement Using Video in Different User States for Online HCI Applications" in Procedia Computer Science 39 (2014), 8 pages.
Starr, "On reading ballistocardiograms*," The American journal of cardiology, vol. 2, No. 4, pp. 404-416, 1958.
Starr, "Essay on the ballistocardiogram," Journal of the American Medical Association, vol. 155, pp. 1413-1425, 1954.
Starr, "Progress towards a physiological cardiology: a second essay on the ballistocardiogram," Annals of internal medicine, vol. 63, No. 6, pp. 1079-1105, 1965.
Starr, "Normal standards for amplitude of ballistocardiograms calibrated by force," Circulation, vol. 11, No. 6, pp. 914-926, Jun. 1955.
Starr, et al., "Studies on the estimation of cardiac output in man, and of abnormalities in cardiac function, from the heart's recoil and the blood's impacts; the ballistocardiogram," American Journal of Physiology, vol. 127, No. 1, pp. 1-28, 1939.
Starr, et al., "Twenty-Year Studies with the Ballistocardiograph the Relation between the Amplitude of the First Record of "Healthy" Adults and Eventual Mortality and Morbidity from Heart Disease," Circulation, vol. 23, pp. 714-732, 1961.
STMicroelectronics. iNEMO inertial module: 3D accelerometer and 3D gyroscope. [Online]. Available: www.st.com/resource/en/datasheet/Ism330.pdf, 2013.
Sun, et al., "Motion-compensated noncontact imaging photoplethysmography to monitor cardiorespiratory status during exercise," Journal of biomedical optics, vol. 16, pp. 077010-077010-9, 2011.
Sun, et al., "Noncontact imaging photoplethysmography to effectively access pulse rate variability," Journal of biomedical optics, vol. 18, pp. 061205-061205, 2013.
Takano, et al., "Heart rate measurement based on a time-lapse image," Medical engineering & physics, vol. 29, pp. 853-857, 2007.
Tarassenko, et al., "Non-contact video-based vital sign monitoring using ambient light and auto-regressive models," Physiological Measurement, vol. 35, p. 807, 2014.
Tavakoli, et al., "An Ultra-Low-Power Pulse Oximeter Implemented With an Energy-Efficient Transimpedance Amplifier," Biomedical Circuits and Systems, IEEE Transactions on, vol. 4, pp. 27-38, 2010.
Thompson, et al., "Ballistocardiography. II. The normal ballistocardiogram," Circulation, vol. 7, No. 3, pp. 321-328, Mar. 1953.
Feng, et al., "Motion-Resistant Remote Imaging Photoplethysmography Based on the Optical Properties of Skin," Circuits and Systems for Video Technology, IEEE Transactions, vol. PP, pp. 1-1, 2014.
Fine, et al., "Multiple scattering effect in transmission pulse oximetry," Medical and Biological Engineering and Computing, vol. 33, pp. 709-712, 1995.
Freitas, "Remote Camera-based Pulse Oximetry," eTELEMED 2014, The Sixth International Conference on eHealth, Telemedicine, and Social Medicine, 2014, pp. 59-63.
Garbey, et al., "Contact-free measurement of cardiac pulse based on the analysis of thermal imagery," Biomedical Engineering, IEEE Transactions, vol. 54, pp. 1418-1426, 2007.
Gesche, et al., "Continuous blood pressure measurement by using the pulse transit time: comparison to a cuff-based method," European Journal of Applied Physiology, vol. 112, pp. 309-315, 2012.
Giovangrandi, et al., "Ballistocardiography—a method worth revisiting," Engineering in Medicine and Biology Society, EMBC, 2011 Annual International Conference of the IEEE, 2011, pp. 4279-4282.
Goedhard, "Ballistocardiography: past, present and future," Bibliotheca cardiologica, pp. 27-45, 1978 (37).

(56) References Cited

OTHER PUBLICATIONS

He, "A wearable heart monitor at the ear using ballistocardiogram (BCG) and electrocardiogram (ECG) with a nanowatt ECG heartbeat detection circuit," Ph.D. dissertation, Electrical Engineering, Massachusetts Institute of Technology, Cambridge, Massachusetts, USA, 2013.

He, et al., "A continuous, wearable, and wireless heart monitor using head ballistocardiogram (BCG) and head electrocardiogram (ECG)," Engineering in Medicine and Biology Society, EMBC, 2011 Annual International Conference of the IEEE, 2011, pp. 4729-4732.

He, et al., "An ear-worn vital signs monitor," IEEE Trans. Biomed. Eng., vol. 62, No. 11, pp. 2547-2552, Oct. 2015.

Henderson, "The mass-movements of the circulation as shown by a recoil curve," American Journal of Physiology—Legacy Content, vol. 14, pp. 287-298, 1905.

Hu, et al., "Feasibility of imaging photoplethysmography," BioMedical Engineering and Informatics, 2008. BMEI 2008. International Conference, 2008, pp. 72-75.

Humphreys, "A CMOS Camera-Based Pulse Oximetry Imaging System," Engineering in Medicine and Biology Society, 2005. IEEE-EMBS 2005. 27th Annual International Conference, 2005, pp. 3494-3497.

Humphreys, et al., "Noncontact simultaneous dual wavelength photoplethysmography: a further step toward noncontact pulse oximetry," Review of Scientific Instruments, vol. 78, p. 044304, 2007.

Inan, et al., "Robust ballistocardiogram acquisition for home monitoring," Physiological measurement, vol. 30(2), p. 169, 2009.

Jackson, et al., "Ballistocardiographic and angiographic correlation study in idiopathic hypertrophic subaortic stenosis," Bibliotheca cardiologica, p. Suppl 27: 14, 1971.

Jago, et al., "Repeatability of peripheral pulse measurements on ears, fingers and toes using photoelectric plethysmography," Clinical Physics and Physiological Measurement, vol. 9, p. 319, 1988.

Jiang, et al., "What is the space of spectral sensitivity functions for digital color cameras?," Applications of Computer Vision (WACV), 2013 IEEE Workshop, 2013, pp. 168-179.

Jin, et al., "A robust image tracker based on phase correlation and Fourier-Mallin transform," Control, Automation and Systems, 2008. ICCAS 2008. International Conference, 2008, pp. 1028-1031.

Johnston, "Development of a Signal Processing Library for Extraction of SpO2, HR, HRV, and RR from Photoplethysmographic Waveforms," Master of Science, Worcester Polytechnic Institute, 2006.

U.S. Appl. No. 16/490,749, filed Sep. 3, 2019.

U.S. Appl. No. 16/526,883, filed Jul. 30, 2019.

Alametsä, et al., "Ballistocardiography in sitting and horizontal positions," Physiological measurement, vol. 29, p. 1071, 2008.

Alametsä, et al., "The potential of EMFi sensors in heart activity monitoring," Proc. 2nd OpenECG Workshop "Integration of the ECG into the HER & Interoperability of ECG Device Systems", Berlin, Germany, 2004.

Asada, et al., Towards the Development of Wearable Blood Pressure Sensors: A Photo-Plethysmograph Approach Using Conducting Polymer Actuators, Engineering in Medicine and Biology Society, 2005. IEEE-EMBS 2005. 27th Annual International Conference, 2005.

Azmal, et al., "Continuous measurement of oxygen saturation level using photoplethysmography signal," Biomedical and Pharmaceutical Engineering, 2006. ICBPE 2006. International Conference, 2006, pp. 504-507.

Baheti, et al., "An ultra low power pulse oximeter sensor based on compressed sensing," Wearable and Implantable Body Sensor Networks, BSN 2009. Sixth International Workshop, 2009, pp. 144-148.

Bal, "Non-contact estimation of heart rate and oxygen saturation using ambient light," Biomedical Optics Express, vol. 6, pp. 86-97, Jan. 1, 2015 2015.

Balakrishnan, et. al, "Detecting pulse from head motions in video," Proc. IEEE Computer Vision and Pattern Recognition (CVPR), Portland, Oregon, USA, 2013, pp. 3430-3437.

Bickler, et al., "Effects of skin pigmentation on pulse oximeter accuracy at low saturation," Anesthesiology, vol. 102, pp. 715-719, Apr. 2005.

Bramwell, et al., "Velocity of transmission of the pulse-wave: and elasticity of arteries," The Lancet, vol. 199, pp. 891-892, 1922.

Brands, et al., "A noninvasive method to estimate pulse wave velocity in arteries locally by means of ultrasound," Ultrasound in medicine & biology, vol. 24, pp. 1325-1335, 1998.

Brüser, et al., "Adaptive beat-to-beat heart rate estimation in ballistocardiograms," Information Technology in Biomedicine, IEEE Transactions, vol. 15, pp. 778-786, 2011.

Burger, et al., "Physical basis of the low-frequency ballistocardiograph," Am. Heart J., vol. 46, No. 1, pp. 71-83, 1953.

Chandrasekaran, Measuring vital signs using smart phones: University of North Texas, 2010.

Chen, et al., "Noninvasive monitoring of blood pressure using optical Ballistocardiography and Photoplethysmograph approaches," Proc. IEEE Eng. Med. Biol. Soc., Osaka, Japan, 2013, pp. 2425-2428.

Coppola, et al., "Signal to noise ratio and response variability measurements in single trial evoked potentials," Electroencephalography and clinical neurophysiology, vol. 44, pp. 214-222, 1978.

Corral Martinez, et al., "Optimal wavelength selection for noncontact reflection photoplethysmography," 2011, pp. 801191-801191-7.

De Haan, et al., "Robust pulse rate from chrominance-based rPPG," Biomedical Engineering, IEEE Transactions, vol. 60, pp. 2878-2886, 2013.

Edwards, "Understanding Continuous Mixed Venous Oxygen Saturation (SvO2) Monitoring with the Swan—Ganz Oximetry TD System 2nd Edition," ed: Edwards Lifesciences, 2002.

Elliott, et al., "Acceleration Ballistocardiography Design, Construction, and Application of a New Instrument," Circulation, vol. 9, No. 2, pp. 281-291, 1954.

Etemadi, et al., "Rapid Assessment of Cardiac Contractility on a Home Bathroom Scale," Information Technology in Biomedicine, IEEE Transactions, vol. 15, No. 6, pp. 864-869, 2011.

Kamat, "Pulse Oximetry," Indian Journal of Anaesthesia, vol. 46, pp. 261-261, Jul. 1, 2002 2002.

Kim, et al., "Signal processing using Fourier wavelet transform for pulse oximetry," Lasers and Electro-Optics, 2001. CLEO/Pacific Rim 2001. The 4th Pacific Rim Conference, 2001, pp. II-II.

Kim, et al., "Ballistocardiogram as proximal timing reference for pulse transit time measurement: potential for cuffless blood pressure monitoring," IEEE Trans. Biomed. Eng., vol. 62, No. 11, Nov. 2015, pp. 2657-2664.

Kong, et al., "Non-contact detection of oxygen saturation based on visible light imaging device using ambient light," Optics Express, vol. 21, pp. 17464-17471, Jul. 29, 2013 2013.

Krug, et al., "Optical ballistocardiography for gating and patient monitoring during MRI: an initial study," Proc. Computing in Cardiology Conference (CinC), Cambridge, Massachusetts, 2014, pp. 953-956.

Kwon, et al., "Validation of heart rate extraction using video imaging on a built-in camera system of a smartphone," in Engineering in Medicine and Biology Society (EMBC), 2012 Annual International Conference of the IEEE, 2012, pp. 2174-2177.

Langewouters, et al., "The static elastic properties of 45 human thoracic and 20 abdominal aortas in vitro and the parameters of a new model," J. Biomech., vol. 17, No. 6, pp. 425-435, 1984.

Lee, et al., "Comparison between red, green and blue light reflection photoplethysmography for heart rate monitoring during motion," Engineering in Medicine and Biology Society (EMBC), 2013 35th Annual International Conference of the IEEE, 2013, pp. 1724-1727.

Lempe, et al., "ROI selection for remote photoplethysmography", In Proc. Bildverarbeitung für die Medizin, 2013, pp. 99-103.

Lucas, et al., "An Iterative Image Registration Technique with an Application to Stereo Vision," Proc. IJCAI, Vancouver, British Columbia, Canada, 1981, pp. 674-679.

(56) References Cited

OTHER PUBLICATIONS

McDuff, et al., "Remote measurement of cognitive stress via heart rate variability," 2014 36th Annual International Conference of the IEEE Engineering in Medicine and Biology Society, 2014, pp. 2957-2960.

Migeotte, et al., "Three dimensional ballistocardiography: methodology and results from microgravity and dry immersion," Engineering in Medicine and Biology Society, EMBC, 2011 Annual International Conference of the IEEE, 2011, pp. 4271-4274.

Moco et al., "Ballistocardiographic artifacts in PPG imaging," IEEE Trans. Biomed. Eng., 2016.

Mukkamala, et al., "Towards ubiquitous blood pressure monitoring via pulse transit time: theory and practice," IEEE Trans. Biomed. Eng., vol. 62, No. 8, pp. 1879-1901, Aug. 2015.

Nihon Kohden Corporation, Half a century of contributing to medical care and society. [Online]. Available: http://www.nihonkohden.com/company/history/ 1950s.html.

Paradiso, "Wearable health care system for vital signs monitoring," Information Technology Applications in Biomedicine, 2003. 4th International IEEE EMBS Special Topic Conference, 2003, pp. 283-286.

Patzak, et al., "Continuous blood pressure measurement using the pulse transit time: comparison to intra-arterial measurement," Blood Press., vol. 24, No. 4, pp. 217-221, Apr. 2015.

Pickett, et al., "Pulse oximetry and PPG measurements in plastic surgery," Engineering in Medicine and Biology Society, 1997. Proceedings of the 19th Annual International Conference of the IEEE, 1997, pp. 2330-2332.

Pinheiro, et al., "Blood pressure and heart rate variabilities estimation using ballistocardiography," In Proceedings of the 7th Conf. on. Telecom, 2009, pp. 125-128.

Pinheiro, et al., "Theory and Developments in an Unobtrusive Cardiovascular System Representation: Ballistocardiography," The Open Biomedical Engineering Journal, vol. 4, pp. 201-216, Oct. 10, 2010.

Poh, et al., "Advancements in noncontact, multiparameter physiological measurements using a webcam," Biomedical Engineering, IEEE Transactions, vol. 58, pp. 7-11, 2011.

Poh, et al., "Non-contact, automated cardiac pulse measurements using video imaging and blind source separation," Optics Express, vol. 18, pp. 10762-10774, May 10, 2010.

Poon, et al., "Wearable intelligent systems for e-health," Journal of Computing Science and Engineering, vol. 5, pp. 246-256, 2011.

PT Direct, Cardiac Output and Blood Pressure, 2016. [Online] Available: https://www.ptdirect.com/training-design/anatomy-and-physiology/cardiac-output-and-blood-pressure.

Rabben, et al., "An ultrasound-based method for determining pulse wave velocity in superficial arteries," Journal of biomechanics, vol. 37, pp. 1615-1622, 2004.

Reisner, et al., "Utility of the photoplethysmogram in circulatory monitoring," The Journal of the American Society of Anesthesiologists, vol. 108, pp. 950-958, 2008.

Rusch, et al., "Alternate pulse oximetry algorithms for SpO<sub>2</sub> computation," Engineering in Medicine and Biology Society, 1994. Engineering Advances: New Opportunities for Biomedical Engineers. Proceedings of the 16th Annual International Conference of the IEEE, 1994, pp. 848-849 vol. 2.

Ngai, et al., "Comparative analysis of seismocardiogram waves with the ultra-low frequency ballistocardiogram," Engineering in Medicine and Biology Society, 2009. EMBC 2009. Annual International Conference of the IEEE, 2009, pp. 2851-2854.

Rusch, et al., "Signal processing methods for pulse oximetry," Computers in Biology and Medicine, vol. 26, pp. 143-159, 1996.

Sachdeva, "Fitzpatrick skin typing: applications in dermatology," Indian Journal of Dermatology, Venereology, and Leprology, vol. 75, No. 1, pp. 93-96, 2009.

Scarborough, et al., "The nature of records from ultra-low frequency ballistocardiographic systems and their relation to circulatory events," The American Journal of Cardiology, vol. 2, pp. 613-641, 1958.

Scarborough, et al., "Proposals for ballistocardiographic nomenclature and conventions: revised and extended report of committee on ballistocardiographic terminology," Circulation, vol. 14, No. 3, pp. 435-450, Sep. 1956.

Scharf, et al., "Optimization of portable pulse oximetry through Fourier analysis," in Biomedical Engineering Conference, 1993., Proceedings of the Twelfth Southern, 1993, pp. 233-235.

Scharf, et al., "Pulse oximetry through spectral analysis," in Biomedical Engineering Conference, 1993., Proceedings of the Twelfth Southern, 1993, pp. 227-229.

Scully, et al., "Physiological Parameter Monitoring from Optical Recordings With a Mobile Phone," Biomedical Engineering, IEEE Transactions, vol. 59, pp. 303-306, 2012.

Shaltis, et al., "Carless blood pressure monitoring using hydrostatic pressure changes," IEEE transactions on biomedical engineering, vol. 55, pp. 1775-1777, 2008.

Shao, et al., "Non-contact monitoring breathing pattern, exhalation flow rate and pulse transit time," IEEE Transactions on Biomedical Engineering, vol. 61, pp. 2760-2767, 2014.

Shao, et al., "Simultaneous Monitoring of Ballistocardiogram and Photoplethysmogram Using Camera," IEEE Transactions on Biomedical Engineering, vol. PP, pp. 1-1, 2016.

Shao, et al., "Noncontact monitoring of blood oxygen saturation using camera and dual-wavelength imaging system," IEEE Trans. Biomed. Eng., vol. 63, No. 6, pp. 1091-1098, Jun. 2016.

Sherwood, "Biology, Human biology," in Human Physiology, From Cells to Systems. 8th ed., Cengage Learning, 2013.

Shi, et al., "Good features to track," Computer Vision and Pattern Recognition, 1994. Proceedings CVPR'94., 1994 IEEE Computer Society Conference, 1994, pp. 593-600.

Shin, et al., "Non-constrained monitoring of systolic blood pressure on a weighing scale," Physiological measurement, vol. 30, No. 7, pp. 679-693, 2009.

Shin, et al., "HRV analysis and blood pressure monitoring on weighing scale using BCG," Proc. IEEE Eng. Med. Biol. Soc., San Diego, California, USA, 2012, pp. 3789-3792.

Sološenko et al., "Photoplethysmography-based method for automatic detection of Premature Ventricular Contractions," IEEE Trans. Biomed. Circuits Syst., vol. 9, No. 5, pp. 662-669, 2015.

Starr, et al., "Ballistocardiogram. II. Normal standards, abnormalities commonly found in diseases of the heart and circulation, and their significance," Journal of Clinical Investigation, vol. 19, No. 3, pp. 437-450, 1940.

Tomasi, et al., "Detection and tracking of point features," Technical Report CMU-CS-91-132, Carnegie Mellon University, Pittsburgh, Pennsylvania, USA, 1991.

Tsai, et al., "A Noncontact Skin Oxygen-Saturation Imaging System for Measuring Human Tissue Oxygen Saturation," Instrumentation and Measurement, IEEE Transactions on, vol. 63, pp. 2620-2631, 2014.

Tsai, et al., "A study on oxygen saturation images constructed from the skin tissue of human hand," in Instrumentation and Measurement Technology Conference (I2MTC), 2013 IEEE International, 2013, pp. 58-62.

Van Brummelen, et al., "On the elimination of pulse wave velocity in stroke vol. determination from the ultralow-frequency displacement ballistocardiogram," Am. Heart. J., vol. 67, No. 3, pp. 374-378, Mar. 1964.

Verkruysse, et al., "Remote plethysmographic imaging using ambient light," Opt. Exp., vol. 16, No. 26, pp. 21434-21445, Dec. 2008.

Voss, et al., "Spontaneous heart rate turbulence in patients with dilated cardiomyopathy," in Proc. IEEE Eng. Med. Biol. Soc., New York City, New York, USA, 2006, pp. 6426-6429.

Wang, et al., "Exploiting spatial redundancy of image sensor for motion robust rppg," IEEE Trans. Biomed. Eng., vol. 62, No. 2, pp. 415-425, Jan. 2015.

Webster, Design of Pulse Oximeters: CRC Press 1997.

Wieringa, et al., "Contactless multiple wavelength photoplethysmographic imaging: a first step toward "SpO2 camera" technology," Annals of biomedical engineering, vol. 33, pp. 1034-1041, 2005.

Winokur, et al., "A wearable vital signs monitor at the ear for continuous heart rate and Pulse Transit Time measurements," Engi-

(56) References Cited

OTHER PUBLICATIONS neering in Medicine and Biology Society (EMBC), 2012 Annual International Conference of the IEEE, 2012, pp. 2724-2727.
Withings Pulse, What does SpO2 mean? What is the normal blood oxygen level? Available: https://withings.zendesk.com/hc/en-us/articles/201494667-What-does-SpO2-mean-What-is-the-normal-blood-oxygen-level, 2015.

* cited by examiner

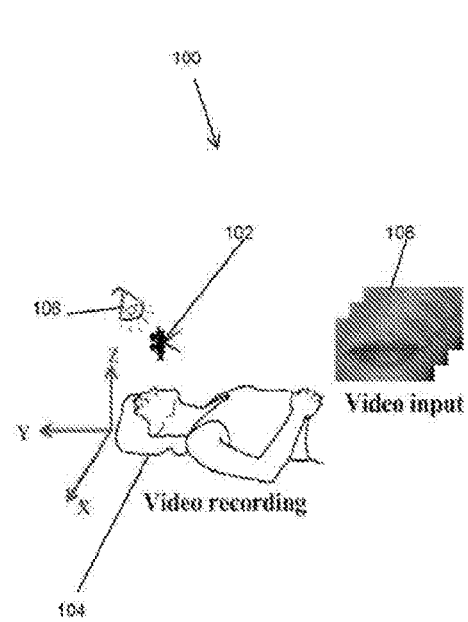
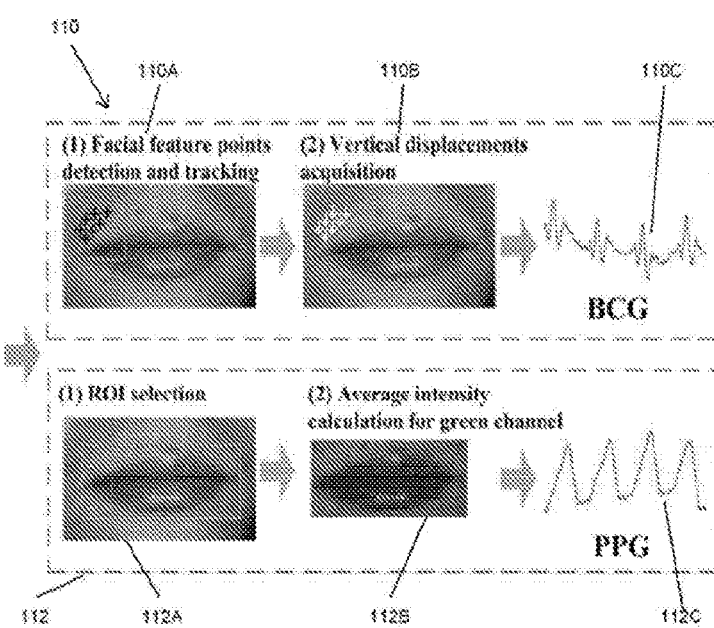
FIG. 1A
FIG. 1B

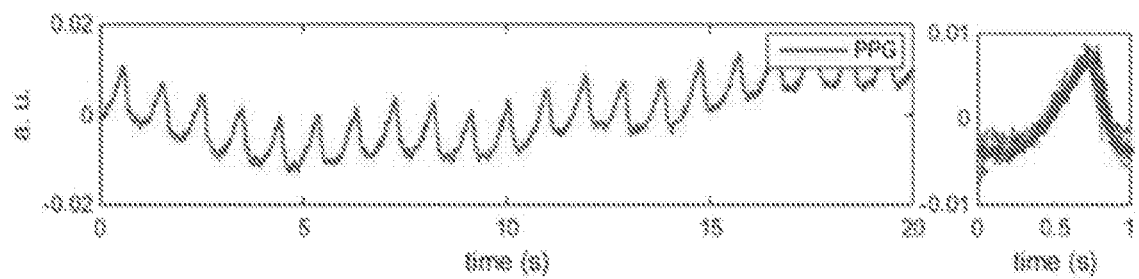
FIG. 3D
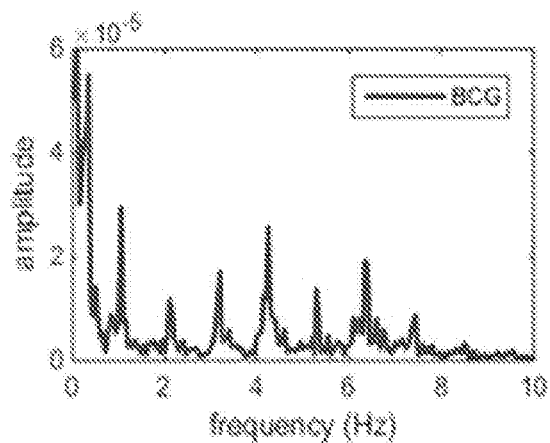 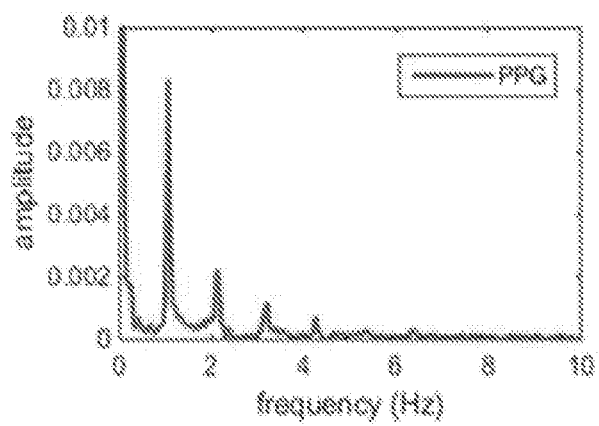
FIG. 3E FIG. 3F

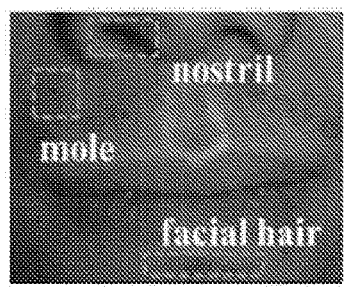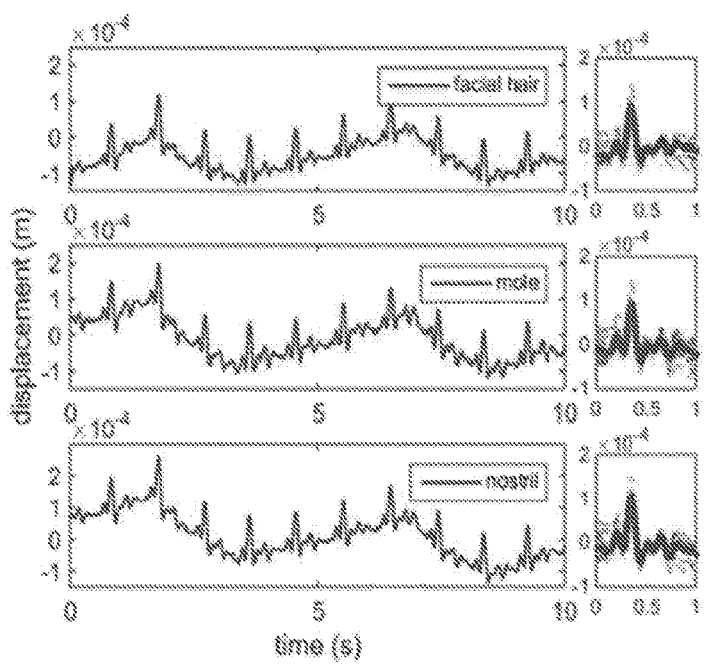
FIG. 4A
FIG. 4B
FIG. 4C
FIG. 4D

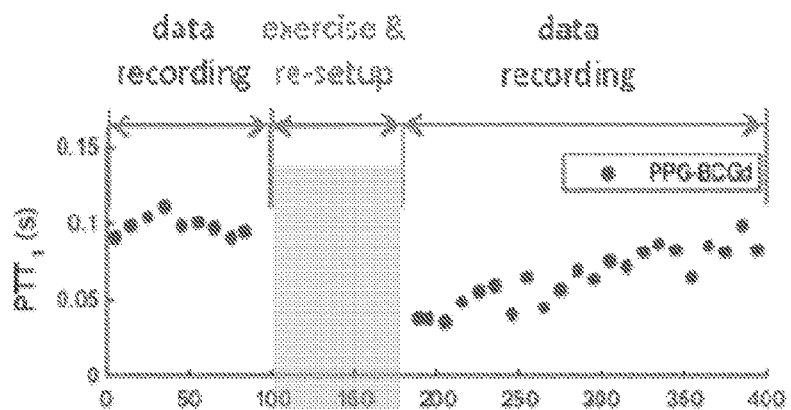
FIG. 18A
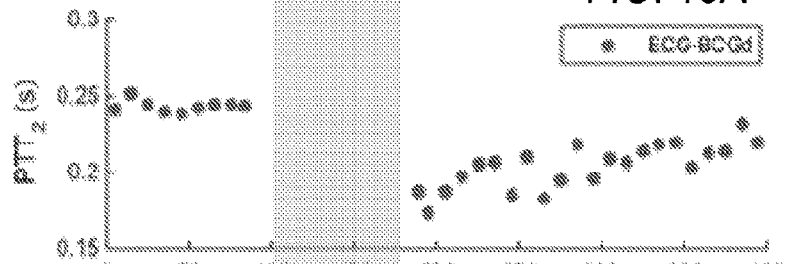
FIG. 18B
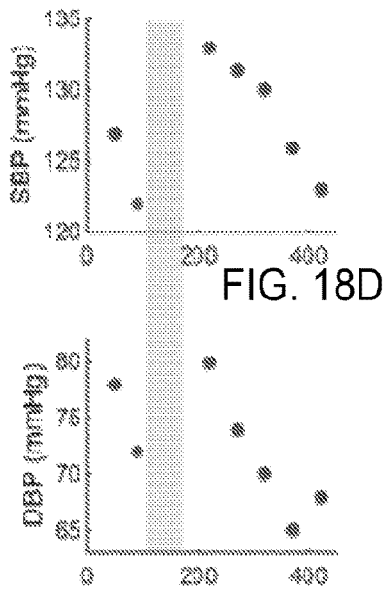
FIG. 18D
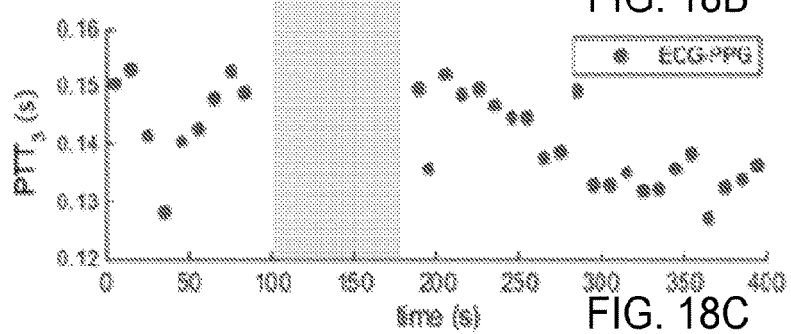
FIG. 18C
FIG. 18E
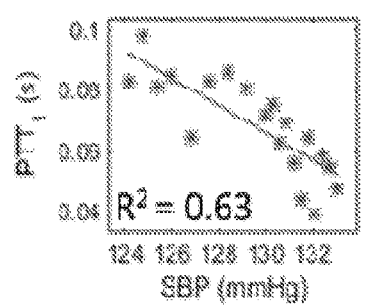
FIG. 18F
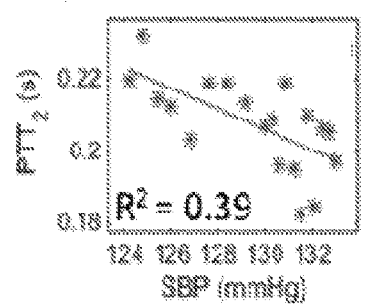
FIG. 18G
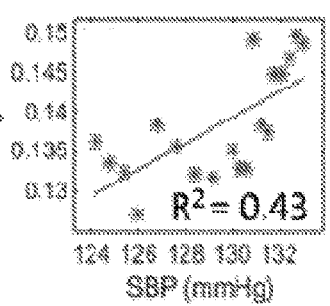
FIG. 18H

SYSTEMS AND METHODS FOR NON-CONTACT MONITORING OF BALLISTOCARDIOGRAM, PHOTOPLETHYSMOGRAM, BLOOD PRESSURE AND ABNORMAL HEART RHYTHM

FIELD

The present disclosure generally relates generally to non-contact and non-invasive monitoring of a subject individual, and in particular to non-contact and non-invasive monitoring of physiological parameters of the subject individual such as ballistocardiogram, photoplethysmogram, pulse transit time, and blood pressure.

BACKGROUND

Ballistocardiogram (BCG) refers to the repetitive body motion generated by cardiac contraction and ejection of blood during cardiac cycles. BCG can be determined from the displacement, velocity or acceleration of body parts, such as head and legs of an individual.

BCG includes important features with physiological relevance, and can be used for idiopathic hypertrophic subaortic stenosis diagnose and early detection of coronary heart disease. For example, the "IJ wave" is a well-accepted method to measure atrial ejection force associated with BCG.

The traditional method to measure BCG is based on a mechanical system, such as a suspended bed, or a suspended rigid platform. Electro kinetic devices based on electrochemical principle to measure BCG are known, but such traditional equipment used in these BCG measurement methods are bulky and complicated, compared with other medical procedures, such as electrocardiography (ECG). As a result, the development and utilization of BCG in health and medical applications has been slow.

Since 2000, with the development of the new sensor technology, BCG has attracted interest again. A research team has developed an ear-worn device that can monitor ECG, BCG and PPG signals together. The BCG signal is obtained from an accelerometer integrated in the device. Other researchers have used a weighing scale installed with a force or pressure sensor to monitor BCG signals, while other researchers have used a polypropylene film coated with electrically conductive layers to measure BCG. However, these aforementioned methods require direct contact of the BCG device with the subject body.

Using a non-contact method to monitor BCG signal has not been well established. Other researchers have reported a method to detect heart rate by tracking the vertical movement of head, but this method does not provide a BCG waveform. In addition, other researchers have used a camera with an MPT marker attached to a user's nasal bridge to track the head movement induced by BCG. Unfortunately, attaching a marker to a person's nose is not practical or at least not desirable. Furthermore, this method also requires that subject to wear a head coil fixated with a cushion to avoid motion artifacts.

Blood pressure is a critical vital sign, which is measured currently with an inflatable cuff; however, the use of an inflatable cuff is inconvenient and also makes it hard to continuously monitor a subject's blood pressure. Different approaches have been attempted to develop cuffless blood pressure measurement. MEMS devices, such as an accelerometer and a conducting polymer actuator, have been used for this purpose. Optical methods based on pulse transit time (PTT) have also been used to infer blood pressure values. PTT is the time required for a pulse signal to travel from one part of the body to another. Most published PTT-based blood pressure monitoring research has focused on the time difference between ECG and photoplethysmogram (PPG) signals. Other researchers have presented a method to monitor blood pressure based on BCG obtained from a microbending fiber sensor, and PPG obtained from a contact-based finger probe. One study used a weighting scale to measure BCG and ECG, and showed that the time interval between these two signals was strongly correlated to cardiac preejection period. These studies suggest that BCG is potentially an alternative to ECG for measuring PTT, and blood pressure, but they all require wearing or using one or more multiple devices in contact with the subject body.

There are also reports on non-contact or imaging-based measurement of PTT based on PPG signals at two different body parts. One study used one camera to record PPT between a subject's face and hand. Another study used one camera to capture blood volume pulses from a subject's face, hand or foot, to extract the corresponding PTT, while another study disclosed the use of the front and back cameras of a smartphone to determine PTT. These conventional systems all require measuring PPG signals from two different body parts. To achieve good accuracy, the two body parts are preferably well separated by a distance, which requires clear imaging of the two body parts; however, this requirement makes it hard to accomplish such clear imaging with a single camera. For example, in one study, the subject must place his/her hand close to the face so that both the hand and face can be clearly imaged. Traditional methods detect premature ventricular contraction (PVC) through ECG measurement to find abnormal heartbeat based on contract-based approach. The electrodes used in ECG are attached to patents' chest directly, which may cause discomfort and skin rashes. Based on the foregoing, there is a need for systems and methods for better non-contact monitoring to determine BCG, PPG, PTT blood pressure and abnormal heart rhythm of a subject individual.

BRIEF DESCRIPTION OF THE DRAWINGS

FIG. 1A is a schematic illustration showing one setup of a non-contact monitoring system for determining BCG and PPG; FIG. 1B is a simplified illustration showing the video input analysis used by the non-contact monitoring system to determine BCG and PPG according to one embodiment.

FIG. 3A-3F are graphical representations of detected signals with corresponding ensemble averages for displacement BCG, velocity BCG, acceleration BCG, PPG, displacement BCG frequency spectrum, and PPG frequency spectrum, according to one aspect of the present disclosure;

FIGS. 4A-4D are graphical representations of BCG waveforms detected from different facial features with corresponding ensemble averages, according to one aspect of the present disclosure;

FIGS. 18A-18H are graphical representations showing PTTs and blood pressure results and correlations from subject number one, according to one aspect of the present disclosure;

Corresponding reference characters indicate corresponding elements among the view of the drawings. The headings used in the figures do not limit the scope of the claims.

DETAILED DESCRIPTION

Figure 1C:
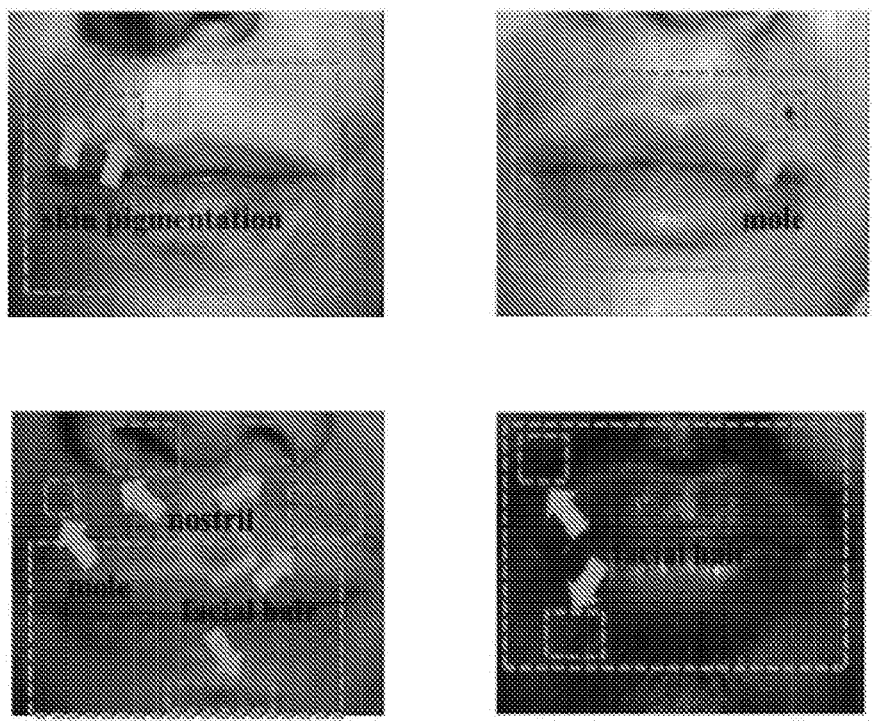
FIG. 1C are images showing regions of interest for BCG (green rectangles) and PPG (blue rectangles) acquisitions, according to one aspect of the present disclosure.

The present disclosure relates to a system and method to simultaneously measure BCG and PPG from the same body part of an individual, such as a face of a subject individual, with optical imaging. In some embodiments, the face or hand of the individual is a preferred body part because the skin of the individual is usually uncovered, allowing for clear imaging of that body part. The regions for the BCG and PPG measurements are preferably the same or close to each region of the individual, which makes it easy to obtain high-resolution optical images with a single camera, and assist to reduce common noise that occurs when measuring several physiological signals from a single region of the individual. The present disclosure further relates to the detection of PPT from the BCG and PPG pulses, and the determination of blood pressure of the subject based on the calculated PTT, together with other physiological parameters, including gender, age, weight and BMI. Referring to the drawings, embodiments of a non-contact monitoring system for determining BCG, PPG, PTT and/or blood pressure and PVC are illustrated and generally indicated as 100 in FIGS. 1-25.

Tracking of PPG and BCG

In some embodiments, the PPG and BCG are determined simultaneously from a similar region of the same body part of an individual, e.g., face, using a single digital camera that records the sequential video images of the particular body part of the individual and communicates those images to a controller. Different imaging and data processing algorithms executed by the controller can be used to determine PPG and BCG, respectively. To determine PPG, the image intensity change of the skin region of the individual's body part is analyzed based on the video images taken by the single digital camera, while to determine BCG, subtle body movements of the individual associated with cardiac activity in the video images are tracked and analyzed. Various algorithms and methods for determining PPG and BCG using the controller are described in greater detail below.

For BCG detection, a region of interest (ROI) is detected, including at least one body feature, such as a facial feature. For each subject, based on his or her personal characteristics, it was found that multiple options of the body feature that could be used to track BCG. Examples of the features that we have successfully used include but not limited to mole, facial hair, nostril, acne, and skin pigmentation. The BCGs from different facial features on the same subject were similar (FIGS. 4A-4D).

Mouth, and its surrounding area, was selected as the ROI due to the availability of abundant distinct facial features for BCG tracking (FIG. 1C). The PPG signal obtained from this ROI was also satisfactory.

Feature points in the defined ROI were detected from the first frame of the video using various methods. The motion of each detected feature point was tracked over video frames with the Kanade-Lucas-Tomasi algorithm (KLT). For an affine motion field $$\delta = Dx + d \quad (1)$$

where d is the translation of the feature window's center and D is the deformation matrix, which is given by $$D = \begin{bmatrix} d_{xx} & d_{xy} \\ d_{yx} & d_{yy} \end{bmatrix}. \quad (2)$$

KLT determines the motion parameters D and d that minimize the dissimilarity e between two adjacent frames, viz. I and J, in a given feature window around position x. e is expressed as $$\varepsilon = \int\int_W \{J[(1+D)x + d] - I(x)\}^2 w(x) dx. \quad (3)$$

The vertical displacement (in the direction along feet to head) contains BCG, which was analyzed in detail. To convert the feature dimensions represented in terms of the number of pixels into meters, a conversion factor was defined as $$\alpha = \frac{\text{feature\_dimension}(m)}{\text{feature\_pixel\_number}(\text{pixel})}. \quad (4)$$

This conversion factor was determined by measuring facial feature dimension (e.g., mouth) using a ruler and counting the pixel numbers of the corresponding feature in the image.

For each frame, n, the vertical components of point locations, $y_b$, were averaged over all the detected feature points, and plotted against time to provide displacement $BCG_d$, which can be written as $$BCG_d(n) = \frac{\sum_{i=1}^{k} y_i(n)}{k} \times \alpha, \quad (5)$$

where k is the number of detected feature points and may vary depending on the type of facial feature.

The first and second temporal derivatives of the displacement BCG were then calculated, leading to velocity $BCG_v$ and acceleration $BCG_a$, respectively.

A method is used to calculate PPG, whereby the image intensity of green and red channels, $I_g$ and $I_r$, were averaged over all the ROI pixels in every frame, and then normalized by the corresponding averages, $\mu(I_g)$, and $\mu(I_r)$, over a time interval, $$PPG(n) = \frac{I_g(n)/\mu(I_g)}{I_r(n)/\mu(I_r)} - 1. \quad (6)$$

This method is less affected by motion compared to the method when a single color channel (e.g., green) is used.

PPG Evaluation

Signal-to-noise ratio (SNR) was analyzed for the measured PPG. A 1200-point FFT was computed and detected the heart rate using peak detection in the frequency domain. The majority of PPG power is found around heart rate (~1 Hz) and its corresponding harmonics. The signal power was then defined as the sum of the squared magnitudes of 5 bins around the heart rate, and 5 bins each around the second and third harmonics. The noise power was the sum of the squared magnitudes of all the other bins in the pulse frequency range (0.5-4 Hz). The ratio of signal power to noise power provided SNR according to $$SNR = 10\log_{10}\left(\frac{\sum_{f=0.5}^{4}(U_t(f)S(f))^2}{\sum_{f=0.5}^{4}(1-U_t(f))S(f))^2}\right) \quad (7)$$

where S(f) is the spectrum of the signal, f is the frequency (Hz), and $U_t(f)$ is a binary window to pass the pulse frequency and isolate the noise frequency.

BCG Feature Extraction and Evaluation

Several features were extracted from measured BCG waveforms, including ensemble averages, IJ intervals and amplitudes. Ensemble averaging was performed over the obtained waveforms to look into the morphology of these signals. In order to obtain the ensemble average, the 20 seconds duration signal was plotted as an eye diagram over one cardiac cycle. Multiple individual cycles (~20 beats) were aligned and then averaged to obtain an ensemble waveform. This is similar to the methods reported in literature to analyze BCG. A time duration of 20 seconds results in adequately stable ensemble waveform. IJ interval was calculated as the time difference between acceleration BCG $I_a$ peak and $J_a$ peak in the same beat, while IJ amplitude was the absolute value of the amplitude from $I_a$ peak to $J_a$ peak.

Compared to PPG, BCG frequency components are more complex and have a wider distribution in the spectrum (FIGS. 3E and 3F). The majority of BCG power stays in the range of 1-10 Hz. Therefore, the SNR of BCG was evaluated based on two methods: one of them employing maximum likelihood and the other using sample correlation coefficient.

SNR estimation based on maximum likelihood can be obtained by:

$$SNR_{ML} = \frac{2\sum_{i=1}^{N} EA_{sub,1}(i)EA_{sub,2}(i)}{\sum_{i=1}^{N}(EA_{sub2}(i) - EA_{sub,2}(i))^2}. \quad (8)$$

where $EA_{sub,1}$ is the sub-ensemble average for the first 10 seconds of the measured displacement BCG, and $EA_{sub,2}$ is that for the remaining 10 seconds. N is the number of samples in the sub-ensemble averages, and i is the sample time index.

Another SNR estimation method is based on sample correlation coefficient r:

$$r = \frac{\sum_{i=1}^{N} EA_{sub,1}(i) EA_{sub,2}(i)}{\sqrt{\sum_{i=1}^{N} EA_{sub,1}(i)^2 \sum_{i=1}^{N} EA_{sub,2}(i)^2}}. \quad (9)$$

The SNR can be then calculated as:

$$SNR_r = A \frac{r}{1-r} + B, \quad (10)$$

where A and B are given by:

$$A = \exp\left(\frac{-2}{N-3}\right), \quad (11)$$

$$B = -\frac{1}{2}\left(1 - \exp\left(\frac{-2}{N-3}\right)\right). \quad (12)$$

To validate the presented BCG detection method for the non-contact monitoring system 100, the measured BCG waveforms were compared against those in literature, and also carried out BCG measurement simultaneously with the accelerometer, which is a well-accepted method for acceleration BCG monitoring. The accelerometer (LSM330) used for the purpose of this study is that found in a commercial off-the-shelf Samsung S4 smartphone. The sample rate of the accelerometer was set at 50 Hz, and based on the datasheet, the linear acceleration sensitivity was typically around 0.007 m/s². The noise level was about 0.005 m/s², which was estimated from the standard deviation by keeping the smartphone stationary on a flat surface for 30 seconds. For measurements with test subjects, the smartphone was placed on the subject's forehead and held in place with a rubber band (FIG. 1A). The y-axis (feet-head direction) acceleration measured by the accelerometer was compared to the vertical acceleration BCG obtained using the presented method. The Pearson's linear correlation coefficients between ensemble averages, IJ amplitudes and intervals obtained using the two methods were calculated.

Pilot Study Participant Information

A small-scale pilot study was carried out to demonstrate the presented video-based method for monitoring BCG and PPG simultaneously. The study included 23 subjects (approved by Institutional Review Board at Arizona State University, No. STUDY00003483). The subjects included 15 males and 8 females of different ages (29±5 years old, mean±SD) and ethnic profiles, and from different regions (North America, South America, East Asia and South India). The skin colors of the subjects ranged from type II (white) to type V (brown) based on the Fitzpatrick scale. Informed consents were obtained from all the subjects following an approved protocol. None of the subjects had any known cardiovascular disease.

A schematic illustration of an experimental setup of one embodiment of the non-contact monitoring system 100 having a controller for determining BCG and PPG shown in FIG. 1A. In some embodiments, a digital camera 102, such as Pike, F-032C digital camera noted above, is used to capture the videos of individual's face 104. In some embodiments, the frame rate can be set at 60 frames per second, although other frame rates may also be used. The video images can be taken by the camera 102 under ambient light condition (e.g., an ordinary 60 W fluorescent lamp). There is no specific requirement on the light source 106 as far as it can provide sufficient illumination of the individual 104 to ensure clear images of the individual's body part 104 (e.g., face) taken by the camera 102. In some embodiments, the individual 104 can stand, sit or lie down on a yoga mat at a distance of approximately 0.5 meters from the lens of the camera 102. Other postures of the individual 104, and distance between the camera 102 and the individual 104 can also be used. The video frames and any associated data are received at the controller, which may implemented by a computer system 200. For example, all the videos and data may be processed and analyzed with software executed by a processor 202 of the computer system 200 shown in FIG. 17 as shall be described in greater detail below.

Figure 2:
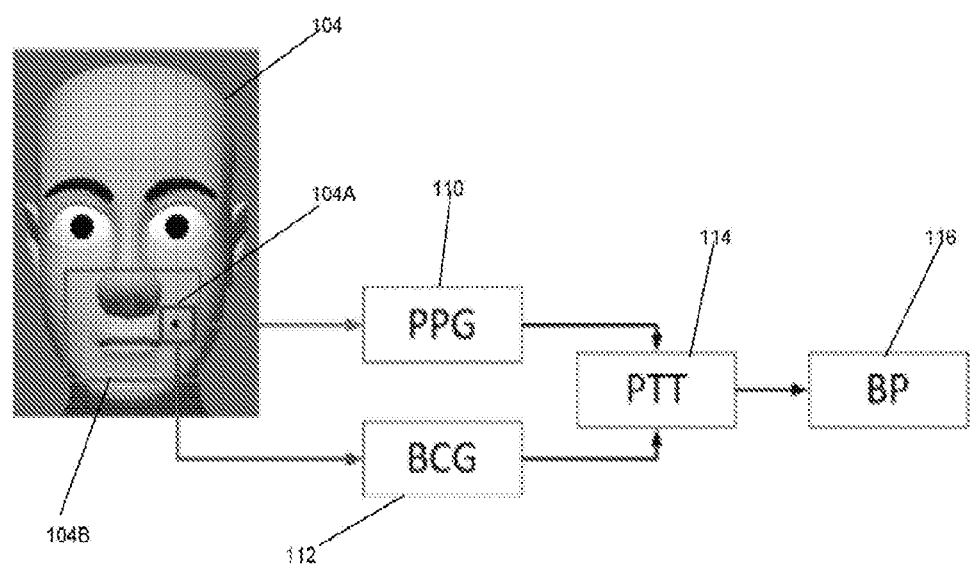
FIG. 2 is a simplified illustration showing one method for non-contact monitoring of blood pressure based on the simultaneous monitoring of BCG and PPG taken from one region of an individual according to one embodiment, according to one aspect of the present disclosure.
Figure 14:
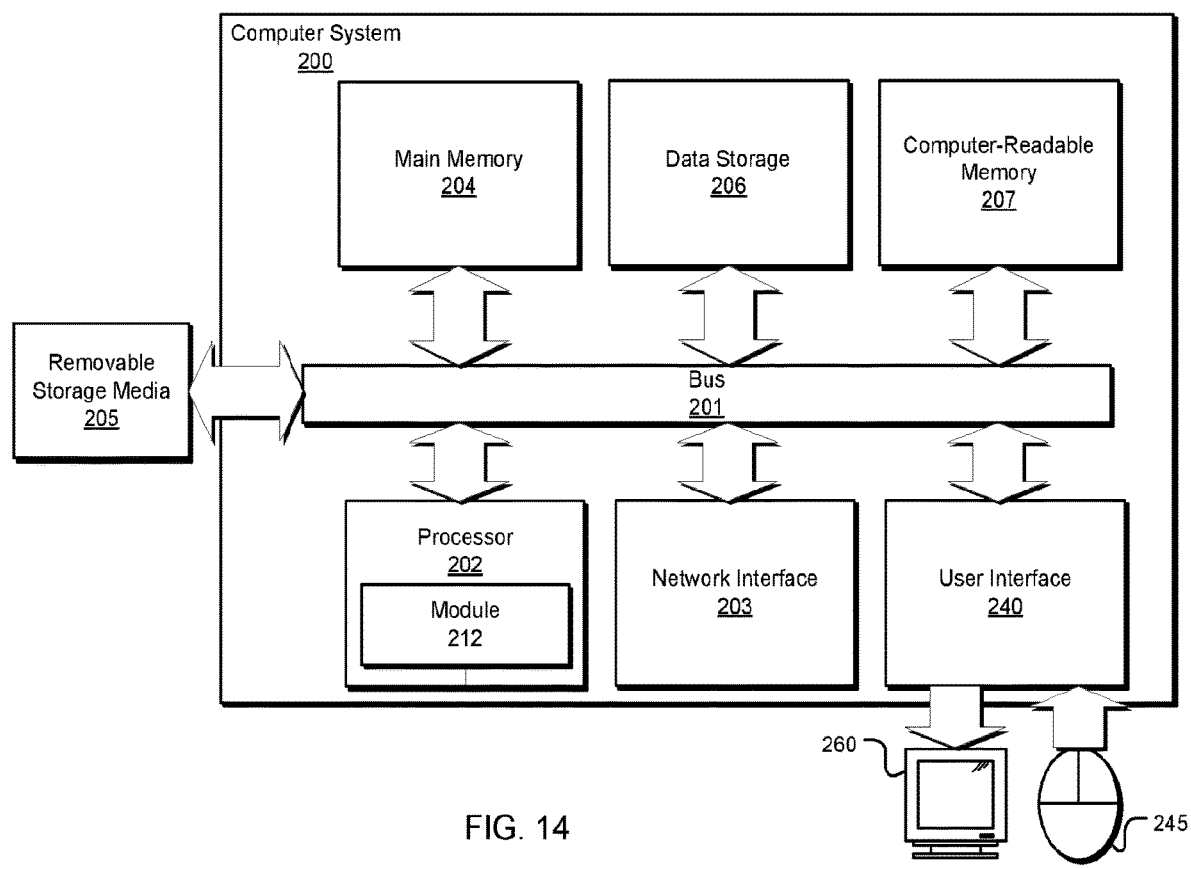
FIG. 14 is a simplified block diagram that illustrates the hardware and software components of the non-contact monitoring system according to one embodiment.

As shown in FIGS. 1B and 2, PPG signals 110 and BCG signals 112 are obtained from the same video of the individual's face 104 taken by the camera 102. The video is recorded for typically about ~30 seconds in each test. After the video is captured, a region of interest (ROI) 104A and 104B on the individual's face 104 is selected to extract PPG signals 110 and BCG signals 112 using the following algorithms discussed below that are executed on the processor 202 (FIG. 14).

PPG Algorithm

Many different algorithms published in literature can be used to determine PPG from the time sequential images (video) of an individual 104. The most straightforward algorithm is used to determine the image intensity averaged over the selection ROI for each frame, and then plot the average intensity vs. time to obtain the PPG signal of the individual.

BCG Algorithm

For BCG detection, a particular feature within the ROI of the face of the individual 104 is selected. Examples of the feature include a mole, nostril, hair and skin texture. After the selection of a face feature, the geometric position of the feature is determined and tracked over time. The geometric position can be described in x, y and z dimensions (FIG. 1A illustrates the definition of the x, y and z directions). In some embodiments, angles may also be included to describe orientation of the feature. The x, y, and z displacements are plotted against time to obtain BCG displacement signals shown in FIG. 14A. The signal in one direction, such as y direction, may be substantially larger than those in other directions. The 1 st-derivative and 2nd-derivative of the acquired BCG displacement signal are calculated as BCG velocity and BCG acceleration signals, respectively.

BCG contains important physiological information. For example, the H peak is related to the motion of the heart early in systole, and the main IJK indicates the ventricular ejection and aortic flow. Specifically, the IJ amplitude reflects ventricular ejection and is highly correlated with stroke volume.

To validate the BCG measurement results, the accelerometer in a Samsung S4 smartphone may be used as a reference. For example, in some embodiments the smartphone may be positioned on the individual's forehead and fixed by an elastic band. The acceleration in x, y and z directions may then be obtained with the y-axis acceleration of the accelerometer representing the vertical movement of the individual 104, which is plotted in FIGS. 14A and 14B for comparison.

Determination of PTT

Once PPG 110 and BCG 112 are determined, PTT 114, the relative time shift between the PPG 110 and BCG 112 pulses is obtained. In some embodiments, one method to determine the PTT 114 (FIG. 2) is determine the position of the most pronounced peak in the BCG signal 112 and the position of the most defined valley in PPG signal 110.

Determination of Blood Pressure

PTT 114 is related to blood pressure, which is one of the most important physiological parameters. However the relation between blood pressure 116 (FIG. 2) and PTT 114 (FIG. 2) may vary with each individual 104. Several factors affect blood pressure 116, including peripheral resistance, vessel elasticity, blood volume and cardiac output. The cardiac output can be calculated from heart rate and stroke volume, where the heart rate can be calculated from either PPG signal 110 or BCG signal 112, and the stroke volume can be found from the BCG signal 112.

In some embodiments, to determine the blood pressure 116 of an individual 104 from PTT 114, it is preferable to include heart rate stroke volume, and other physiological parameters from BCG 112 and PPG 110 in the formulism. In some embodiments, accurate measurement of blood pressure 116 from PTT 114 may include calibration with a reference technology, such as traditional blood pressure equipment. In some embodiments, another calibration method may use the blood pressure 116 change when the individual 104 changes his/her position from lying flat to sitting up.

In other embodiments, a different approach to determine blood pressure 116 from PTT 114 is to create a model that relates blood pressure to PTT 114, age, gender, weight and height of the individual 104, as well as heart rate stroke volume, and other physiological parameters determined from BCG signals 112 and PPG signals 110. This approach does not require calibration, but it will be based on a large cohort study to establish the model.

Initial Test Results

BCG and PPG

Figure 3A:
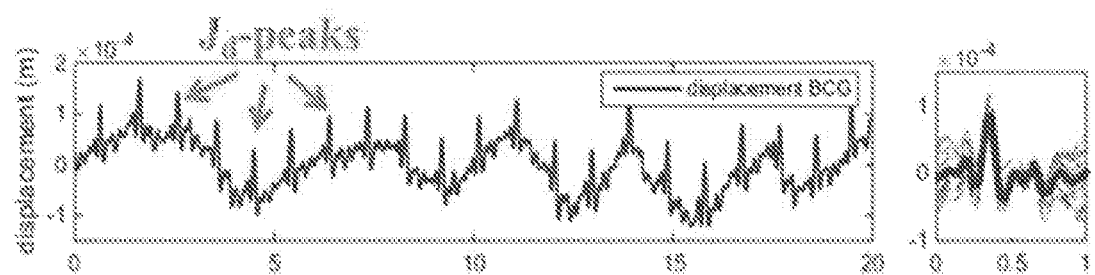
Figure 3B:
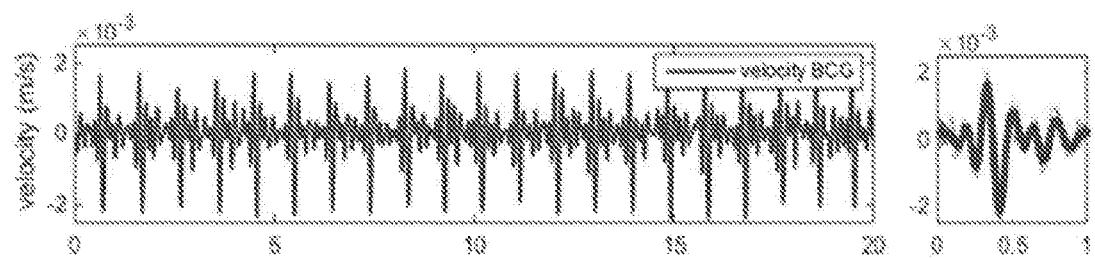
Figure 3C:
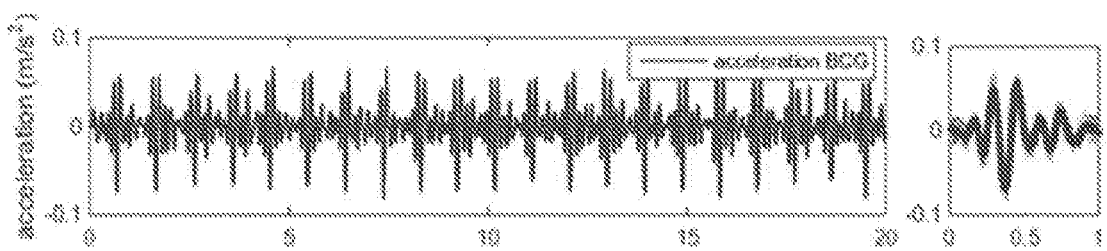

The displacement BCG and PPG simultaneously was obtained from a video of each subject. FIGS. 3A-3F show the results for a male subject. The $J_d$-peak, one of the most prominent features of BCG, is clearly resolved in the displacement BCG obtained with the presented video method (FIG. 3A). The corresponding velocity and acceleration BCGs were obtained by taking first and second temporal derivatives, and then filtering them with a $2^{nd}$ order Butterworth filter with a passband of [0.5, 10] Hz (FIG. 3A and FIG. 3C). The obtained PPG is shown in FIG. 3D). DC bias is removed from these signals. Ensemble averages of these waveforms are provided on the right of the figures. The power spectra of the displacement BCG and PPG are shown in FIGS. 3E and 3F).

FIGS. 4A-4D show the BCGs detected from three different facial features (facial hair, mole and nostril) using the same video of a male subject. BCGs obtained from different features look very similar. The Pearson's linear correlation coefficients between every two signals are larger than 0.95, implying that the displacement BCGs obtained from the three features are strongly correlated.

Validation of BCG Detection

To validate the video-based noncontact method for BCG detection, simultaneous measurement of BCG with a reference device (accelerometer) were carried out. The acceleration BCGs along feet-head direction obtained using the present method, and the reference methods are plotted in FIGS. 5A-5D. Both waveforms are filtered with a $2^{nd}$ order Butterworth filter with a passband of [0.5, 10] Hz. The obtained BCG waveform from the video is resampled from 60 Hz to 50 Hz to match the sampling rate of the accelerometer for comparison purpose. The overall patterns and the obtained cardiac cycles from the two methods are consistent with each other, which validates the presented noncontact method for BCG monitoring.

Figure 5A:
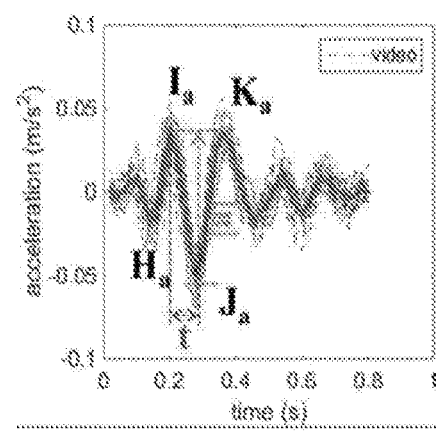
FIGS. 5A-5D are graphical representations showing the comparison of acceleration BCG waveforms obtained with the non-contact monitoring system, according to one aspect of the present disclosure.
Figure 5B:
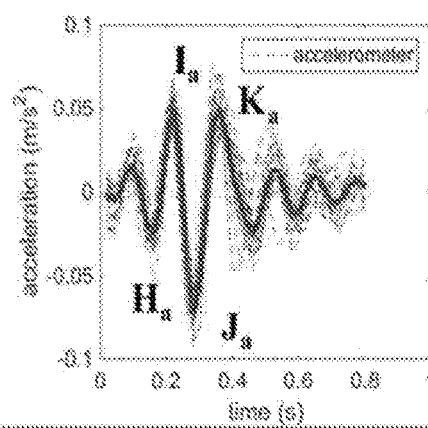
Figure 5C:
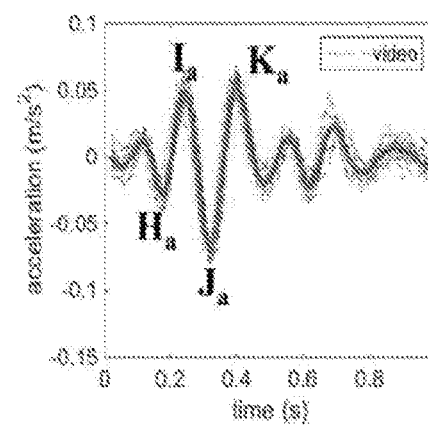
Figure 5D:
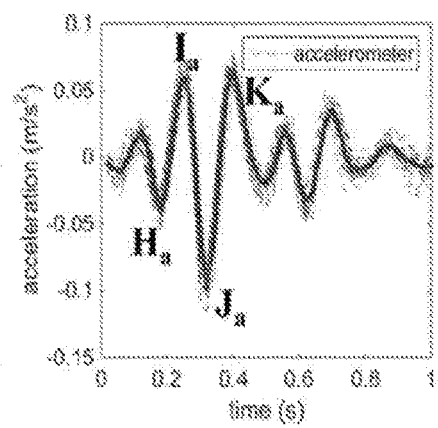

To further examine the detailed features of the BCGs obtained with the two methods, ensemble averaging was performed for two subjects over a duration of 20 seconds, and the resulting waveforms, including individual cycles (dash lines) and ensemble averages (solid lines), are shown in FIGS. 5A-5D. (solid line). The major waves (H, I, J, and K), IJ amplitude (|a|), and IJ interval (t) are denoted with letters, FIG. 5B illustrates BCG for the female subject shown in FIG. 5A, measured simultaneously using an accelerometer. FIG. 5C illustrates BCG waveforms, for a male subject (heart rate=1.1 Hz), measured from 19 individual cardiac cycles (dash lines) and ensemble average for the 19 cycles (solid line). FIG. 5D illustrates the BCG for the male subject shown in FIG. 5C, measured simultaneously using an accelerometer.

For both subjects, the major peaks in BCG waveforms from the presented and reference methods are similar, and the Pearson's linear correlation coefficients are larger than 0.95, implying that the test results obtained from the two methods are strongly related. Furthermore, the obtained BCGs from both methods are also consistent with the typical direct body measurement BCG waveforms reported in literature.

Small Scale Pilot Study

Figure 6:
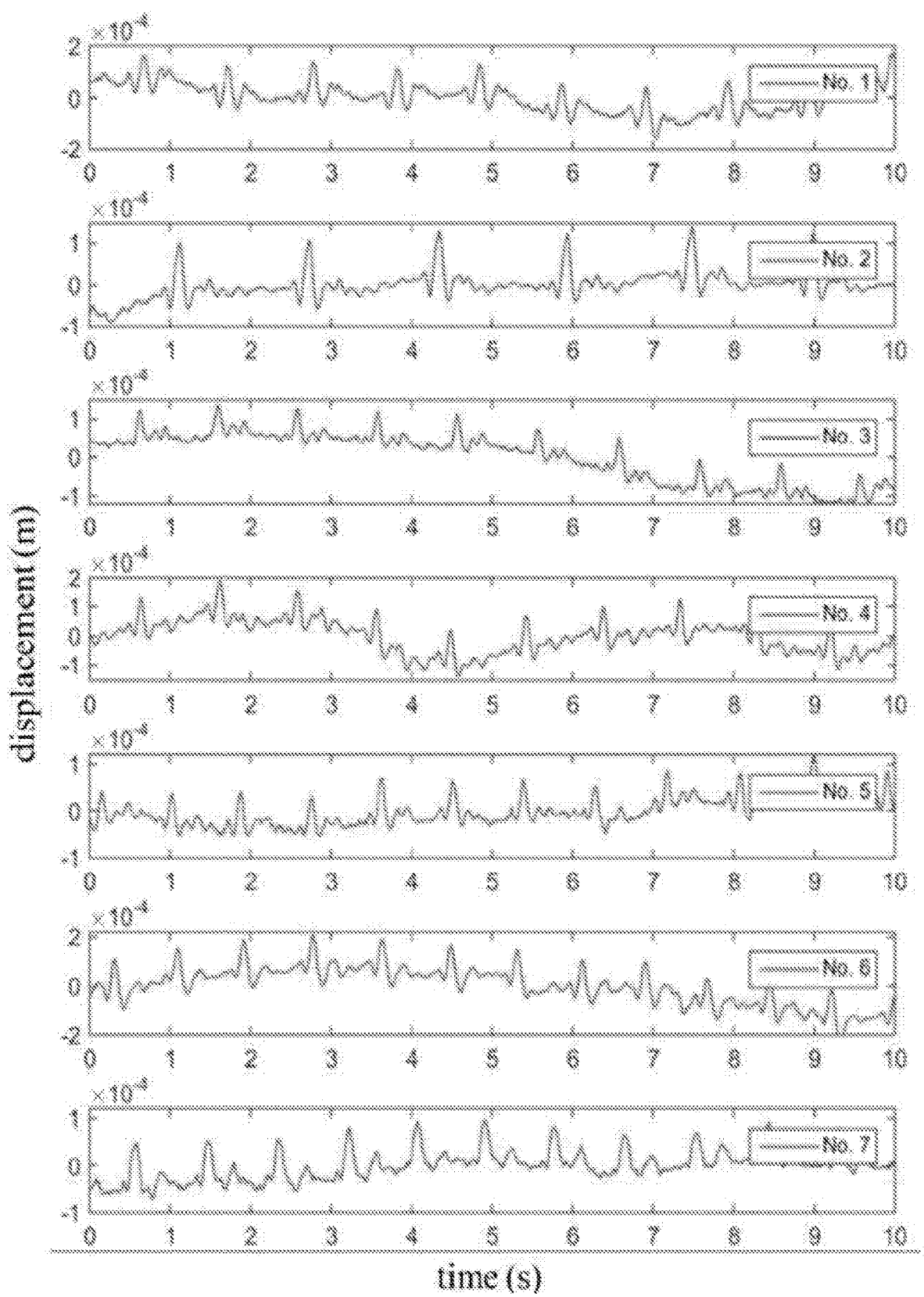
FIG. 6 is a graphical representation of displacement BCGs obtained from different subjects, according to one aspect of the present disclosure.

In the small-scale pilot study, a test was performed as described in above on each subject. FIG. 6 shows the displacement BCGs obtained from seven different subjects for the purpose of demonstration. The overall BCG waveforms are similar for all subjects, but the detailed features show substantial variations due to different physiological attributes, which have also been reported by other literatures. The largest amplitudes of the measured displacement BCG J-peaks ranged from $1\times10^{-4}$ to $2\times10^{-4}$ m. The velocity and acceleration peaks varied from $2\times10^{-3}$ to $6\times10^{-3}$ m/s, and 0.05 to 0.15 m/s$^2$, respectively. These values are comparable to those reported by other researchers using different methods (Table 1). For the same subject, the measurement error for these values was about 10% in consecutive tests.

TABLE 1

BCG VALUES COMPARISON

| BCG Type | References | Presented Method |
|---|---|---|
| displacement (m) | $6 \times 10^{-5}$ [28], $1.5 \times 10^{-4}$ [50], $10^{-4}$ [45] | $1.5 \times 10^{-4}$ |
| velocity (m/s) | $2.5 \times 10^{-3}$ [28], | $4 \times 10^{-4}$ |
| acceleration (m/s$^2$) | 0.1 [9, 17], 0.08 [45] | 0.09 |

The reference values are estimated from the report test results (plots). The values from the presented method are averaged over 23 healthy subjects.

Figure 7:
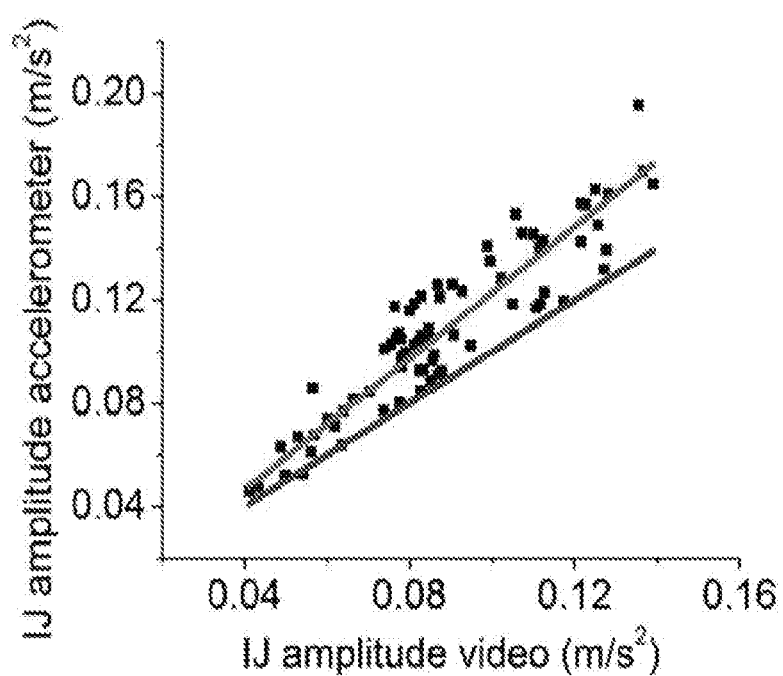
FIG. 7 is a graphical representation of the correlation between the IJ amplitudes of BCGs obtained using the non-contact monitoring system, according to one aspect of the present disclosure.
Figure 8:
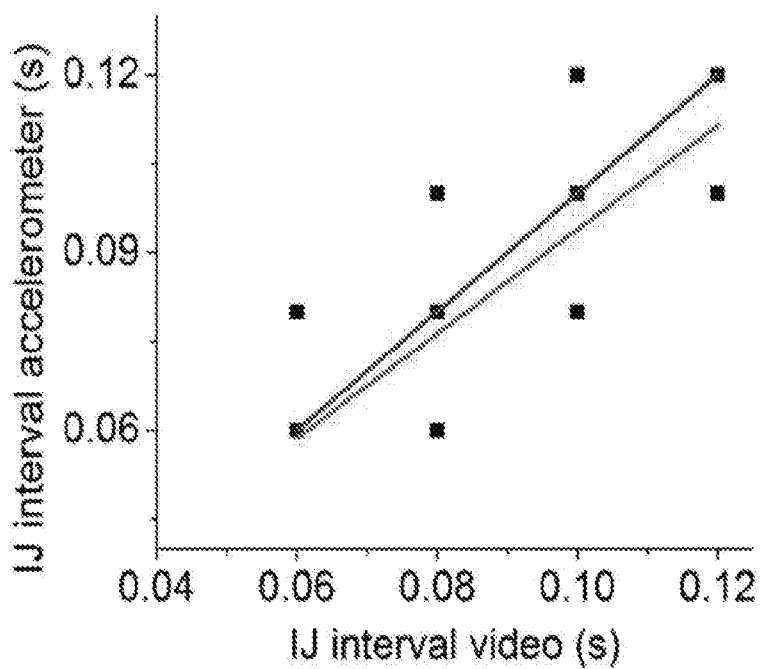
FIG. 8 is a graphical representation of the correlation between the IJ intervals of acceleration BCGs obtained using the non-contact monitoring system, according to one aspect of the present disclosure.

The IJ amplitudes (|a|) and intervals (t) of acceleration BCGs determined using the non-contact monitoring system were compared with those using the reference accelerometer. FIGS. 7 and 8 show the plots of these two values from 73 tests with linear least square regression. Good linear correlation is found between the presented and reference methods for both plots ($R^2=0.82$ and $R^2=0.7$). The difference between the two methods may be attributed to different body locations (mouth region for presented method and forehead for accelerometer). The accuracy may also be affected by the calibration error.

Figure 9:
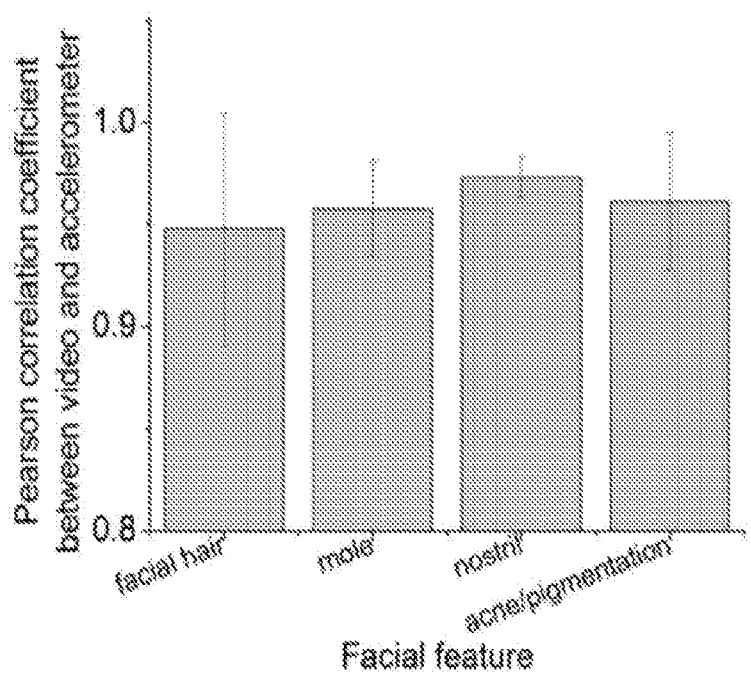
FIG. 9 is a graphical representation of the Pearson correlation coefficients between the non-contact monitoring system and the reference device with different facial features, according to one aspect of the present disclosure.
Figure 10:
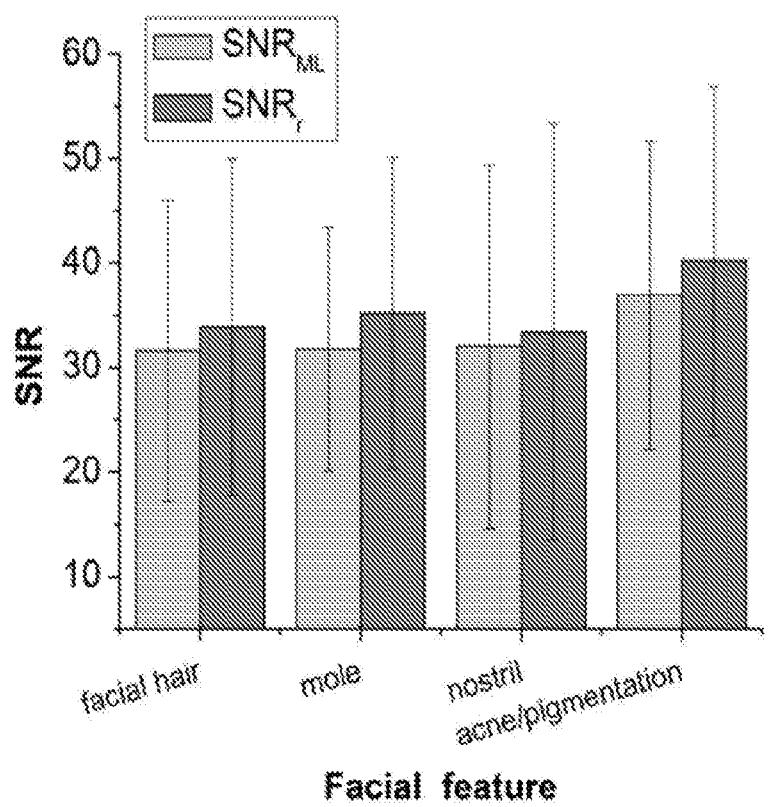
FIG. 10 is a graphical representation of the SNR estimation of BCG using the non-contact monitoring system, with standard deviation, based on the maximum likelihood ($SNR_{ML}$) and sample correlation coefficient ($SNR_p$), according to one aspect of the present disclosure.

FIG. 9 summarizes the Pearson's linear correlation coefficients between the BCGs measured using the presented method and reference accelerometer. FIG. 10 shows the BCG SNR values based on maximum likelihood (8) and sample correlation coefficient (10) using the presented method. All the test results are divided into four groups based on the types of facial features used for motion tracking. The SNR values and the standard deviations are comparable using weighing scale. FIGS. 9 and 10 suggest that the selection of facial features is not a key factor for video-based BCG monitoring since the values are comparable among different features.

Figure 11:
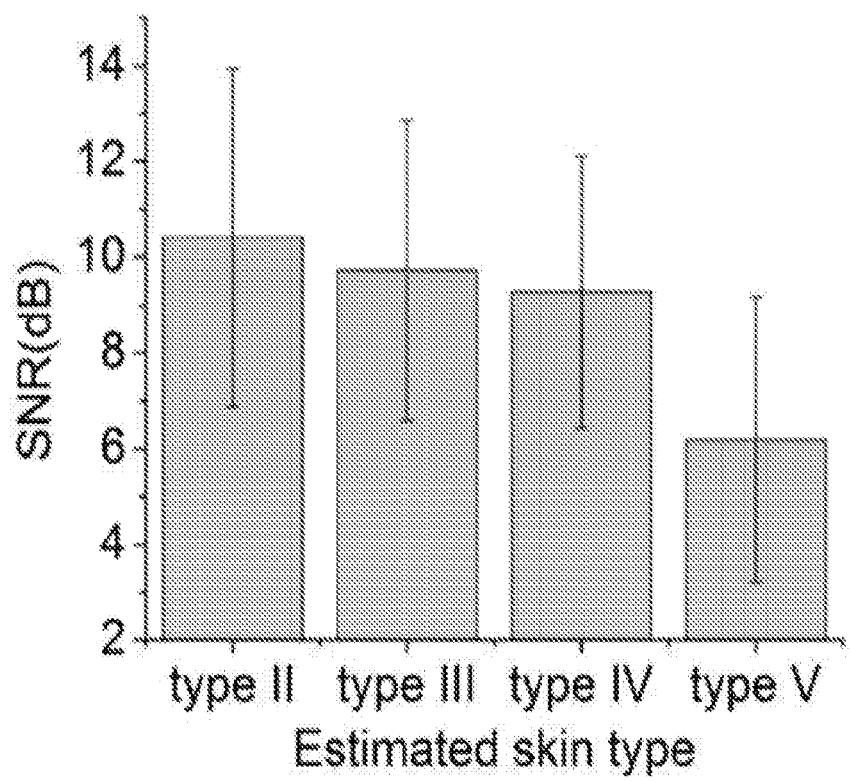
FIG. 11 is a graphical representation of SNR of PPG form different skin categories with standard deviation, according to one aspect of the present disclosure.
Figure 12A:
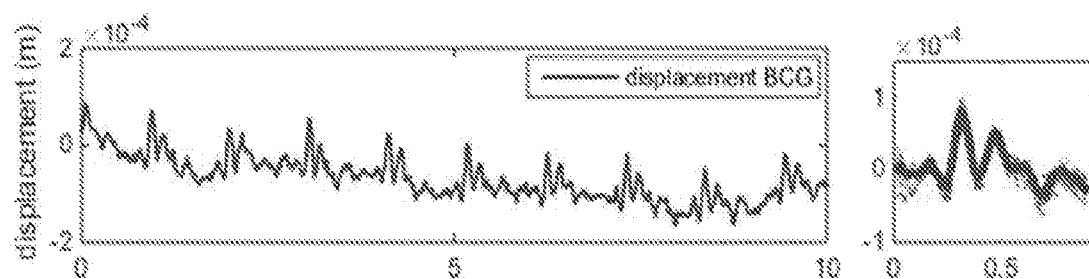
FIGS. 12A-12E are graphical representations of detected signals with corresponding ensemble averages for displacement BCG, velocity BCG, acceleration BCG, PPG from video-based method, PPG, and acceleration BCG from a reference device when the subject is at a sitting position, according to one aspect of the present disclosure.
Figure 12B:
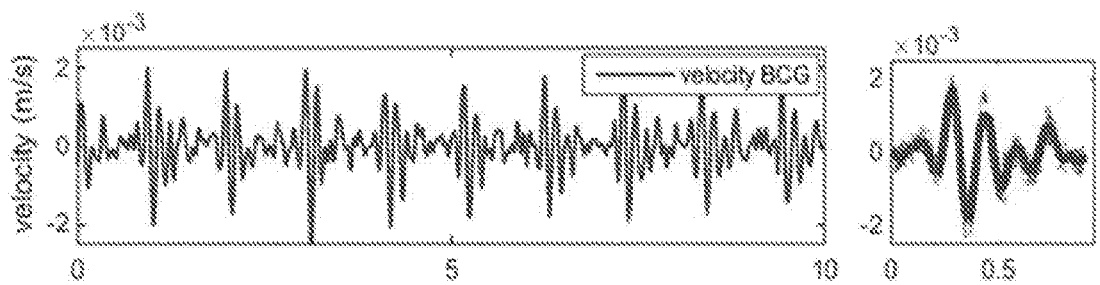
Figure 12C:
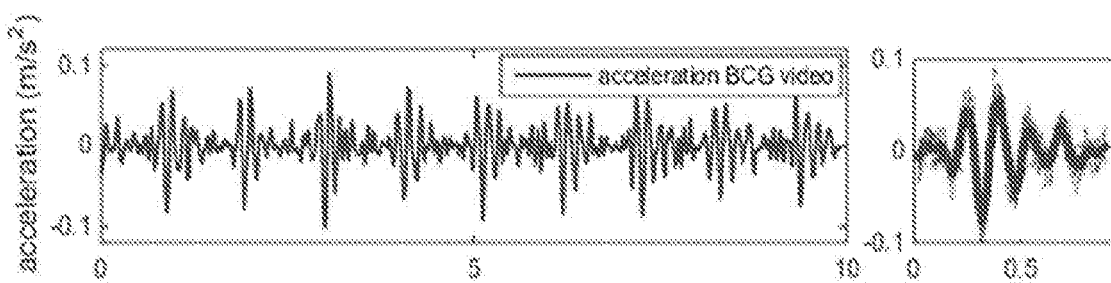
Figure 12D:
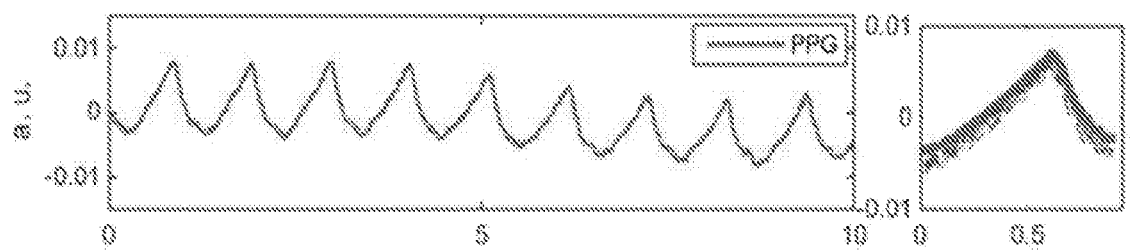
Figure 12E:
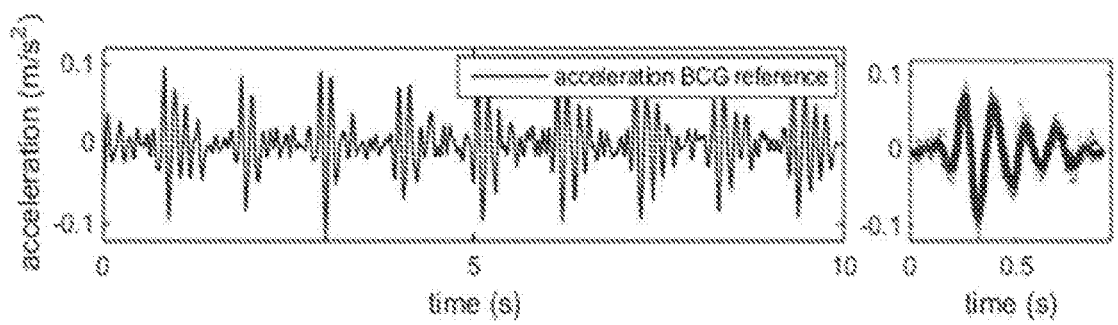
Figure 13A:
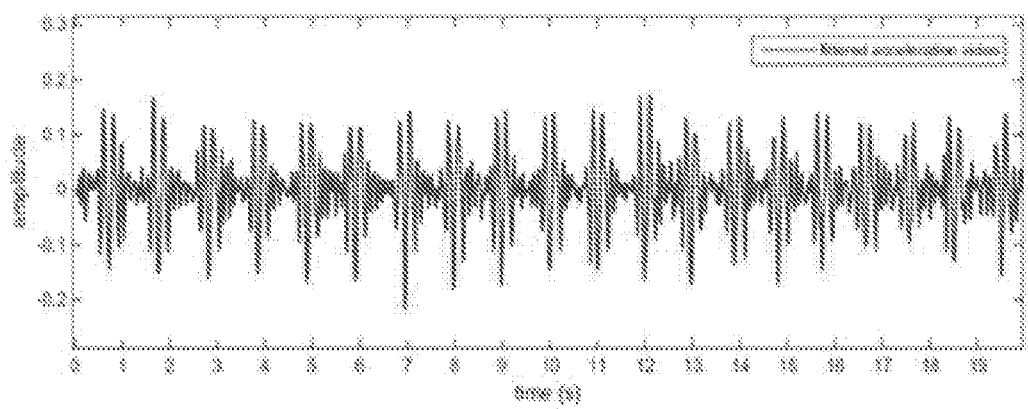
FIGS. 13A and 13B are graphs showing a comparison of BCG detection from a video-based method and an accelerometer-based method according to one embodiment.
Figure 13B:
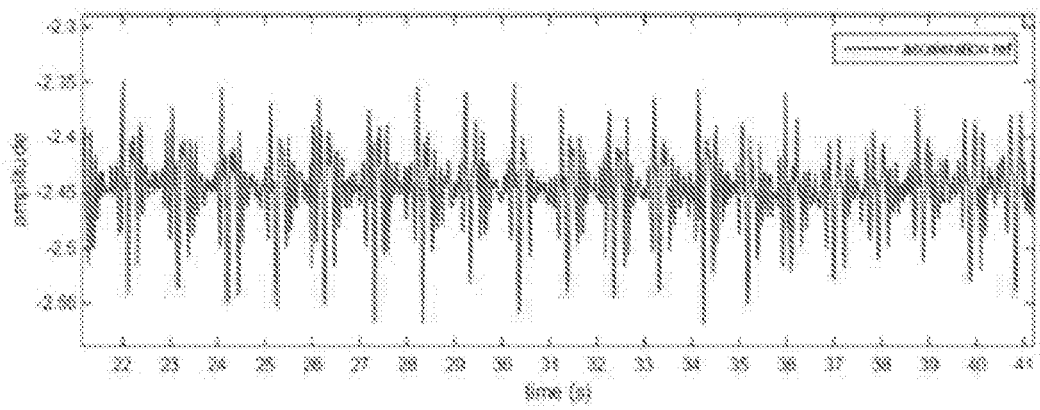

To evaluate PPG quality, we plotted the PPG SNR, as shown in FIG. 11. All the test results are divided into four different skin types. The overall SNR values are comparable to other studies. The SNR values from lighter skin tone subjects are better than darker skin tone subjects, which have also been reported by other researchers.

Signals from Other Posture

The non-contact monitoring system was validated against a sitting position of the subject. For example, FIGS. 12A-12E. illustrate the signals obtained when the subject was sitting on a chair. BCG was obtained by tracking facial feature (mole) and PPG was obtained from the mouth region, using the same methods as described above. The subject was the same as the one in FIGS. 3A-3D. An accelerometer was also used as a reference device for comparison. The Pearson's linear correlation coefficient between the presented method (FIG. 12C) and reference device (FIG. 12E) was shown to be 0.97. BCG waveforms show the difference between sitting and supine positions, which has also been reported in other literature.

FIG. 14 illustrates an example of a suitable computing and networking environment used to implement various aspects of the present disclosure. Example embodiments described herein may be implemented at least in part in electronic circuitry; in computer hardware executing firmware and/or software instructions; and/or in combinations thereof. Example embodiments also may be implemented using a computer program product (e.g., a computer program tangibly or non-transitorily embodied in a machine-readable medium and including instructions for execution by, or to control the operation of, a data processing apparatus, such as, for example, one or more programmable processors or computers). A computer program may be written in any form of programming language, including compiled or interpreted languages, and may be deployed in any form, including as a stand-alone program or as a subroutine or other unit suitable for use in a computing environment. Also, a computer program can be deployed to be executed on one computer, or to be executed on multiple computers at one site or distributed across multiple sites and interconnected by a communication network.

Certain embodiments are described herein as including one or more modules. Such modules are hardware-implemented, and thus include at least one tangible unit capable of performing certain operations and may be configured or arranged in a certain manner. For example, a hardware-implemented module may comprise dedicated circuitry that is permanently configured (e.g., as a special-purpose processor, such as a field-programmable gate array (FPGA) or an application-specific integrated circuit (ASIC)) to perform certain operations. A hardware-implemented module may also comprise programmable circuitry (e.g., as encompassed within a general-purpose processor or other programmable processor) that is temporarily configured by software or firmware to perform certain operations. In some example embodiments, one or more computer systems (e.g., a stand-alone system, a client and/or server computer system, or a peer-to-peer computer system) or one or more processors may be configured by software (e.g., an application or application portion) as a hardware-implemented module that operates to perform certain operations as described herein.

Accordingly, the term "hardware-implemented module" encompasses a tangible entity, be that an entity that is physically constructed, permanently configured (e.g., hardwired), or temporarily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules 212 at different times. Software may accordingly configure a processor 202, for example, to constitute a particular hardware-implemented module at one instance of time and to constitute a different hardware-implemented module at a different instance of time.

Hardware-implemented modules 212 may provide information to, and/or receive information from, other hardware-implemented modules 212. Accordingly, the described hardware-implemented modules 212 may be regarded as being communicatively coupled. Where multiple of such hardware-implemented modules 212 exist contemporaneously, communications may be achieved through signal transmission (e.g., over appropriate circuits and buses) that connect the hardware-implemented modules. In embodiments in which multiple hardware-implemented modules 212 are configured or instantiated at different times, communications between such hardware-implemented modules may be achieved, for example, through the storage and retrieval of information in memory structures to which the multiple hardware-implemented modules 212 have access. For example, one hardware-implemented module 212 may perform an operation, and may store the output of that operation in a memory device to which it is communicatively coupled. A further hardware-implemented module 212 may then, at a later time, access the memory device to retrieve and process the stored output. Hardware-implemented modules 212 may also initiate communications with input or output devices.

As illustrated, the computing and networking environment 200 may a general purpose computing device 200, although it is contemplated that the networking environment 200 may include other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the general purpose computing device 200 may include various hardware components, such as a processing unit 202, a main memory 204 (e.g., a system memory), and a system bus 201 that couples various system components of the general purpose computing device 200 to the processing unit 202. The system bus 201 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The general purpose computing device 200 may further include a variety of computer-readable media 207 that includes removable/non-removable media and volatile/non-volatile media, but excludes transitory propagated signals. Computer-readable media 207 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the general purpose computing device 200. Communication media includes computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The main memory 204 includes computer storage media in the form of volatile/nonvolatile memory such as read only memory (ROM) and random access memory (RAM). A basic input/output system (BIOS), containing the basic routines that help to transfer information between elements within the general purpose computing device 200 (e.g., during start-up) is typically stored in ROM. RAM typically contains data and/or program modules that are immediately accessible to and/or presently being operated on by processing unit 202. For example, in one embodiment, data storage 206 holds an operating system, application programs, and other program modules and program data.

Data storage 206 may also include other removable/non-removable, volatile/nonvolatile computer storage media. For example, data storage 206 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media provide storage of computer-readable instructions, data structures, program modules and other data for the general purpose computing device 200.

A user may enter commands and information through a user interface 240 or other input devices 245 such as a tablet, electronic digitizer, a microphone, keyboard, and/or pointing device, commonly referred to as mouse, trackball or touch pad. Other input devices 245 may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices 245 are often connected to the processing unit 202 through a user interface 240 that is coupled to the system bus 201, but may be connected by other interface and bus structures, such as a parallel port, game port or a universal serial bus (USB). A monitor 260 or other type of display device is also connected to the system bus 201 via user interface 240, such as a video interface. The monitor 260 may also be integrated with a touch-screen panel or the like.

The general purpose computing device 200 may operate in a networked or cloud-computing environment using logical connections of a network Interface 203 to one or more remote devices, such as a remote computer. The remote computer may be a personal computer, a server, a router, a network PC, a peer device or other common network node, and typically includes many or all of the elements described above relative to the general purpose computing device 200. The logical connection may include one or more local area networks (LAN) and one or more wide area networks (WAN), but may also include other networks. Such networking environments are commonplace in offices, enterprise-wide computer networks, intranets and the Internet.

When used in a networked or cloud-computing environment, the general purpose computing device 200 may be connected to a public and/or private network through the network interface 203. In such embodiments, a modem or other means for establishing communications over the network is connected to the system bus 201 via the network interface 203 or other appropriate mechanism. A wireless networking component including an interface and antenna may be coupled through a suitable device such as an access point or peer computer to a network. In a networked environment, program modules depicted relative to the general purpose computing device 200, or portions thereof, may be stored in the remote memory storage device.

Figure 15:
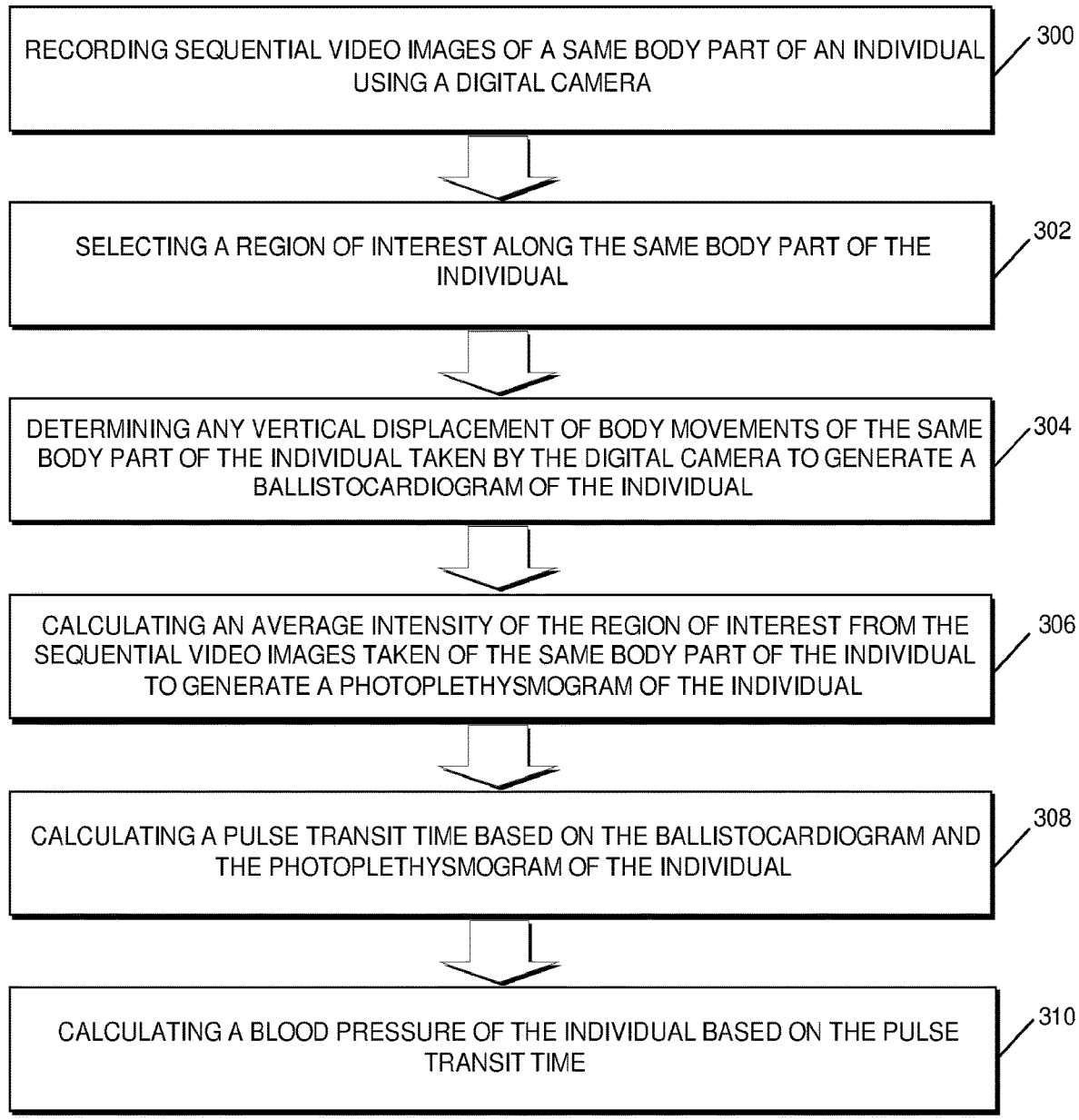
FIG. 15 is a flow chart illustrating a method for determining BCG and PPG using the non-contact monitoring system according to one embodiment.
Figure 16:
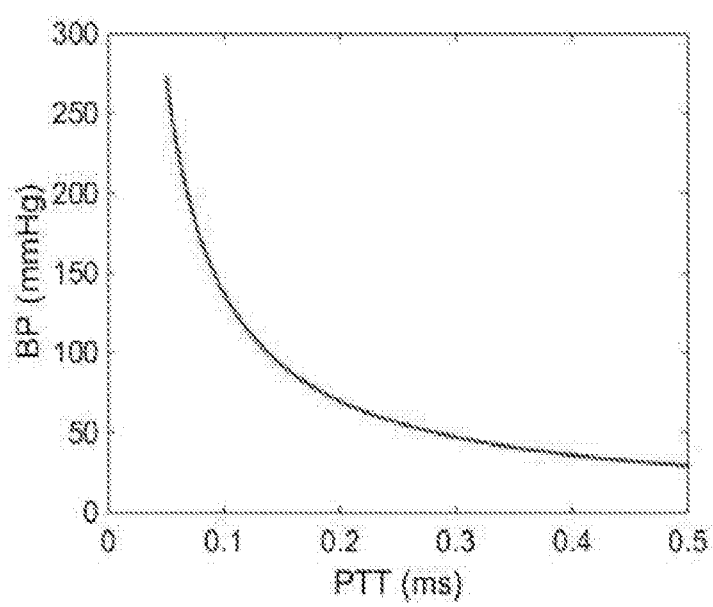
FIG. 16 shows the relationship between PTT and blood pressure, according to one aspect of the present disclosure.

Referring to FIG. 15, a flow chart illustrates the operation of one method performed by the controller, including the hardware-implemented module 212 executed by the processor 202 of the computing device 200 to simultaneously measure BCG and PPG from the same body part of an individual as illustrated in FIG. 1B. At block 300, recording sequential video images 108 of a same body part of an individual using digital camera 102. At block 302, selecting a region of interest 112A along the same body part of the individual. At block 304, tracking body movements 110A of the same body part of the individual in the sequential video images 108 taken by the digital camera 102. At block 304, determining any vertical displacements 110B of body movements of the same body part of the individual in the sequential video images 108 taken by the digital camera 102 to generate a BCG 110C of the individual. At block 306, calculating an average intensity 112B of the region of interest from the sequential video images 108 taken of the same body part of the individual to generate a PPG 112C of the individual. At block 308, calculating a pulse transit time based on the BCG 110C and PPG 112C. At block 310, calculating a blood pressure of the individual based on the pulse transit time.

Relationship Between Pulse Transit Time and Blood Pressure

The relationship between PTT and BP has been analyzed with the arterial wall model and the arterial wave propagation model. If the arterial vessel is modeled as an elastic cylindrical tube, then PTT can be regarded as the time for a pressure wave to travel along the tube over a distance of l. This leads to, $$\text{PTT} = l\sqrt{\rho C/A} \qquad (13)$$

where $\rho$ is blood density, A is the vessel cross-sectional area, and C is compliance that measures the blood vessel's ability to resist pressure. Pressure (P) can be expressed in terms of PTT as, $$P = P_1\sqrt{\frac{A_m \cdot \rho \cdot l^2}{\pi A \cdot P_1 \cdot PTT^2} - 1} + P_0 \qquad (14)$$

where $A_m$, $P_0$ and $P_1$ are subject-specific parameters and where $A_m$, $P_0$ and $P_1$ are subject-specific parameters. If we assume the values of the parameters based on reference, an inverse correlation can be found between PTT and BP in FIG. 16.

Other researchers have also reported BP can be empirically correlated with PTT with different equations such as $$BP = K_1 \ln(PTT) + K_2, \qquad (15)$$

$$BP = \frac{K_1}{PTT} + K_2, \qquad (16)$$

$$BP = \frac{K_1}{(PTT - K_2)^2} + K_3, \qquad (17)$$

where K are subject-specific parameters [100]. Therefore, it is expected to see some dependence between BP and PTT.

Method of Measurement

A Pike camera (F-032C) was used to monitor PPG and BCG, meanwhile EPIC Sensors (PS25451) were used to monitor ECG as a reference cardiac signal. Prominent features of these signals were identified by the time they occurred in each cardiac cycle. The features included: ECG "R" peak, PPG peak and displacement BCG "$J_d$" peak. The time difference was estimated between every two signals in each cardiac cycle, which included: (1) $PTT_1$: time delay from displacement BCG "$J_d$" peak to PPG peak; (2) $PTT_2$: time delay from ECG "R" peak to displacement BCG "$J_d$" peak; and (3) $PTT_3$: time delay from ECG "R" peak to PPG peak. The obtained time delays were plotted against time. Within these values, $PTT_1$ can be obtained by using camera. Obtained PTT values were averaged every 10 seconds to reduce the influence of artifacts (e.g. respiration). A commercial cuff-based blood pressure monitor (Omron BP786) was used as reference to record BP values about every 40-50 seconds. The measurement error of the reference BP monitor is about ±5 mmHg.

Design of Experiment

To validate the presented method for blood pressure tracking, the subjects were asked to do exercises to alter their blood pressure. Researchers have reported that systolic blood pressure (SBP) is inversely correlated with PTT after exercise. Depending on the effort level and body condition of the subjects, SBP was changed from 5 to 30 mmHg, and diastolic blood pressure (DBP) was changed from 1 to 10 mmHg. Based on literature, SBP correlates better with PTT compared with DBP.

Each experiment had five stages including a 400-second video recording. The five stages (FIG. 20) are as follows:

Stage I: System setup (120 seconds). The subject is asked to lie down and maintain a relaxed state. Camera was adjusted to a proper view with good focus for video recording. Two ECG electrodes were connected to the skin. Reference BP monitor is attached to subject's upper arm through a cuff.

Stage II: Resting 1 (100 seconds). Video and ECG data are recorded simultaneously. Reference BP monitors measures the BP values every 40-50 seconds.

Stage III: Exercise (60 seconds). The subject was asked to take moderate exercise (sit up or push up) for about 1 minute.

Stage IV: Re-setup (20-60 seconds). The subject was asked to lie down and relax. Camera, ECG sensors and reference BP monitor were set up again to measure corresponding values from subject after taking exercise. The re-setup is tried to be done as soon as possible, normally it takes about 20-60 seconds.

Stage V: Resting 2 (~200 seconds). The non-contact monitoring system 100 resumed collecting data till the end of the experiment.

Figure 17:
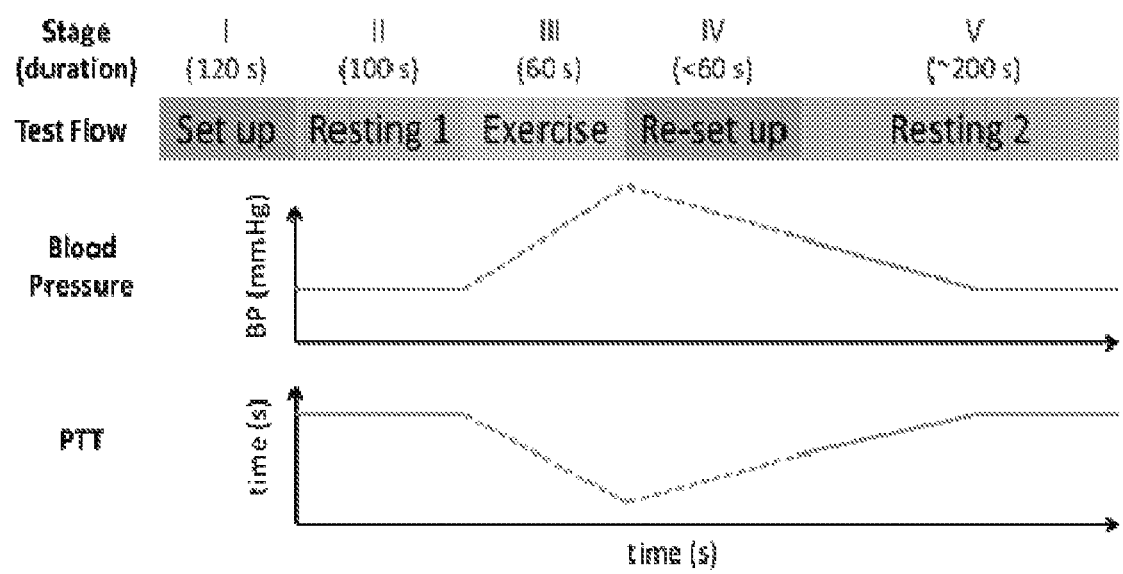
FIG. 17 is a graphical representation showing the experiment workflow and estimated changes in blood pressure and PTT, according to one aspect of the present disclosure.
Figures 19A, 19B, 19C, 19D, 19E, 19F, 19G, 19H:
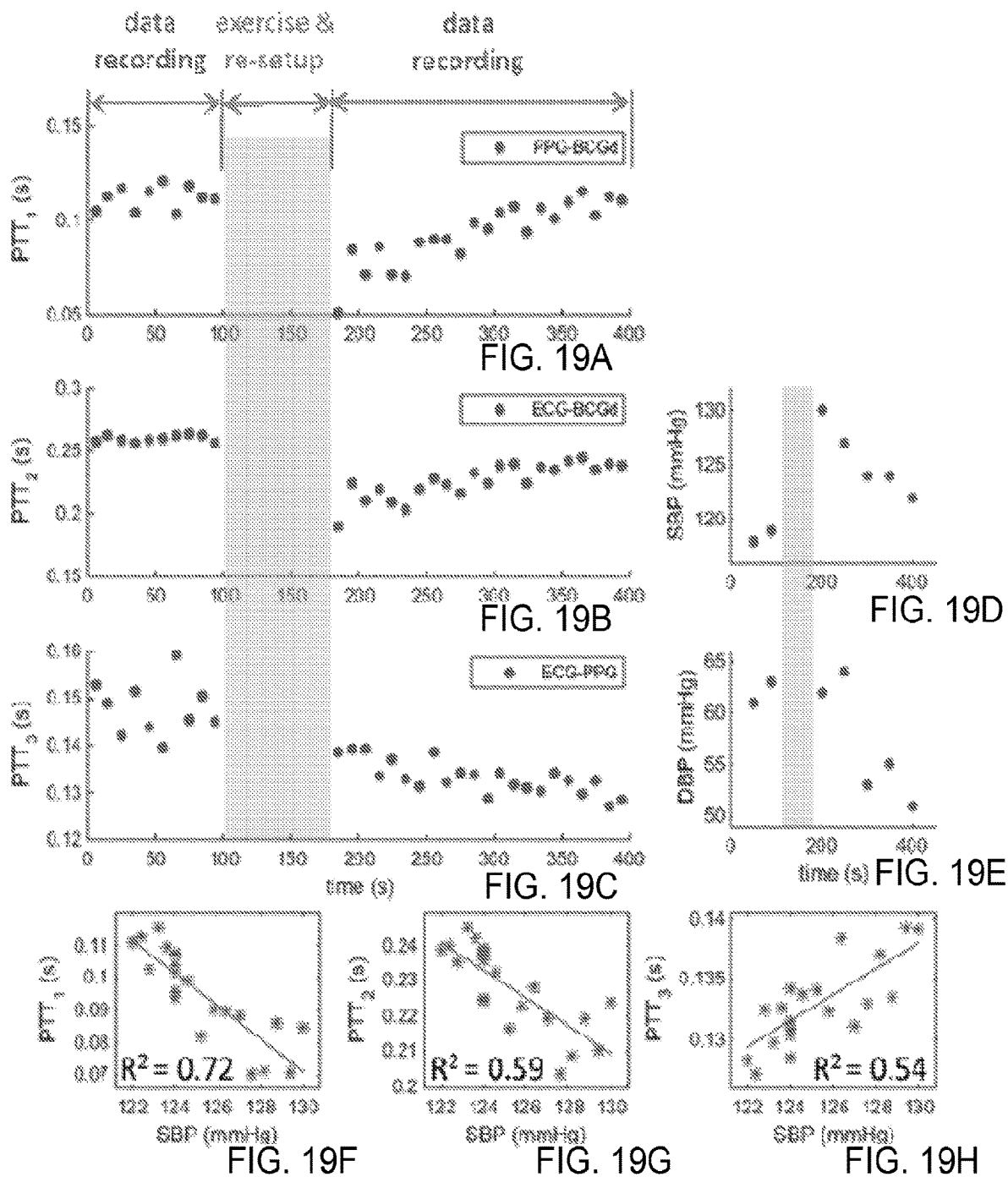
FIGS. 19A-19H are graphical representations showing PTTs and blood pressure results and correlations from subject number two, according to one aspect of the present disclosure.
Figures 20A, 20B, 20C, 20D, 20E, 20F, 20G, 20H:
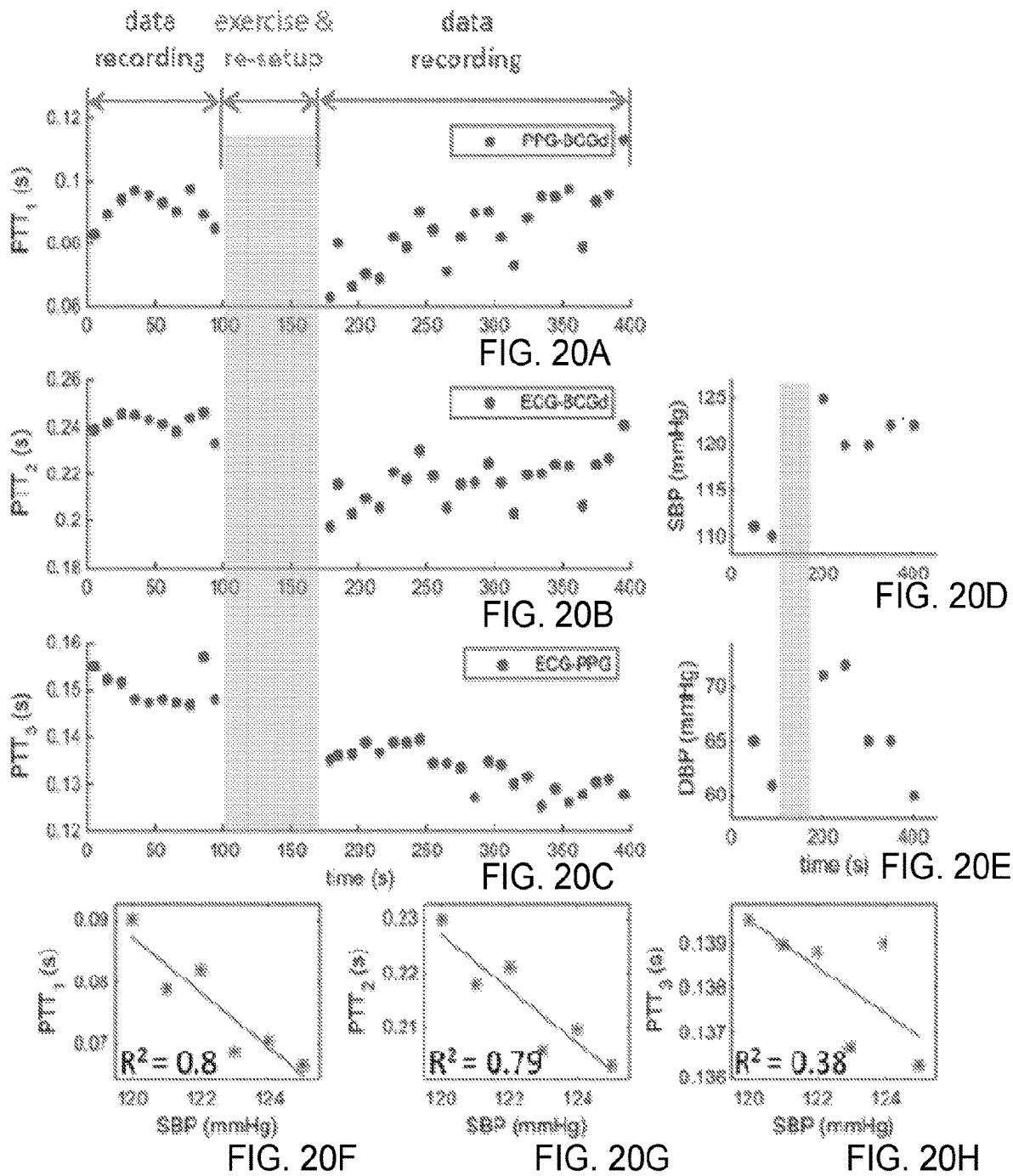
FIGS. 20A-20H are graphical representations showing PTTs and blood pressure results and correlations from subject number three, according to one aspect of the present disclosure.
Figures 21A, 21B, 21C, 21D, 21E, 21F, 21G, 21H:
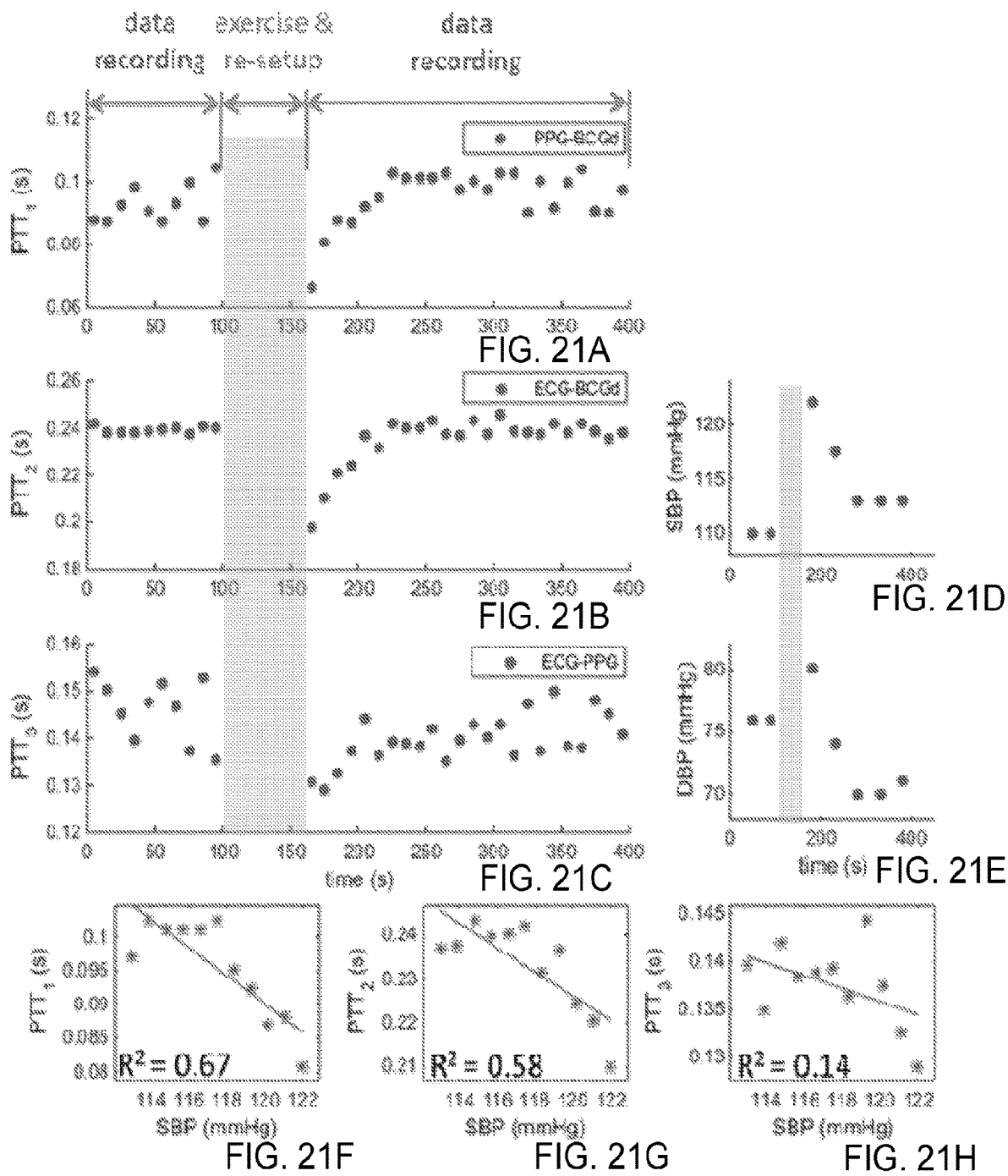
FIGS. 21A-21H are graphical representations showing PTTs and blood pressure results and correlations from subject number four, according to one aspect of the present disclosure.
Figure 22A:
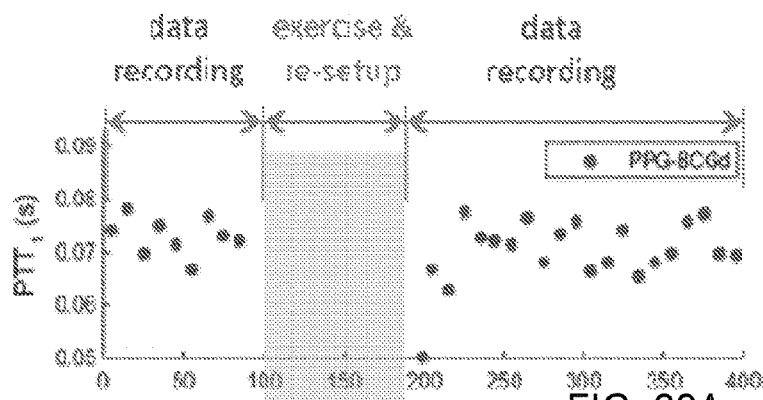
FIGS. 22A-22H are graphical representations showing PTTs and blood pressure results and correlations from subject number five, according to one aspect of the present disclosure.
Figure 22B:
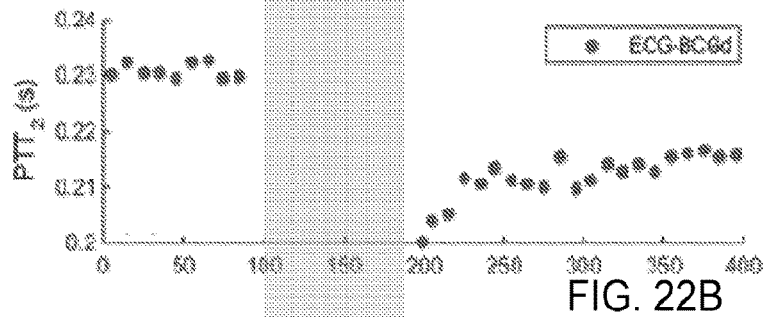
Figure 22D:
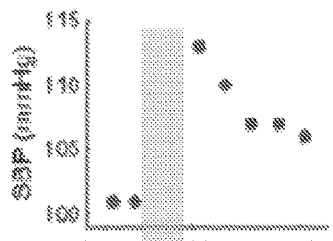
Figure 22C:
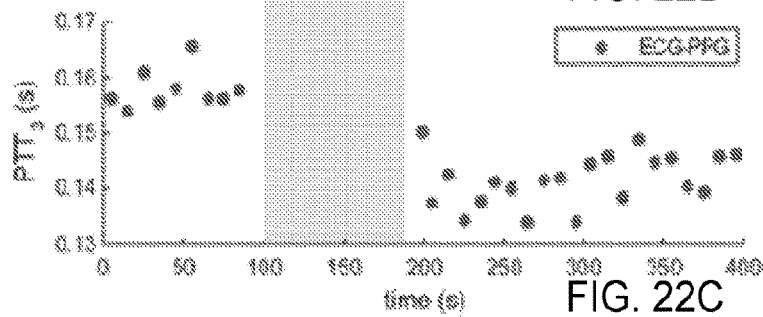
Figure 22E:
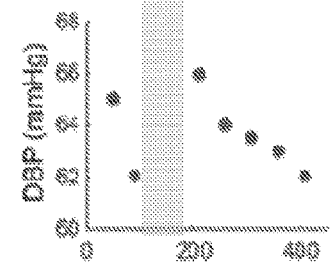
Figure 22F:
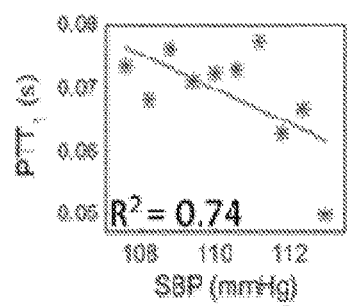
Figure 22G:
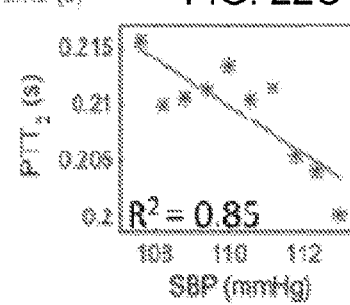
Figure 22H:
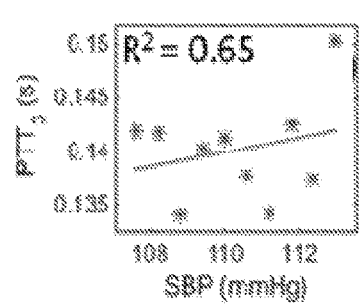
Figures 23A, 23B, 23C, 23D, 23E, 23F, 23G, 23H:
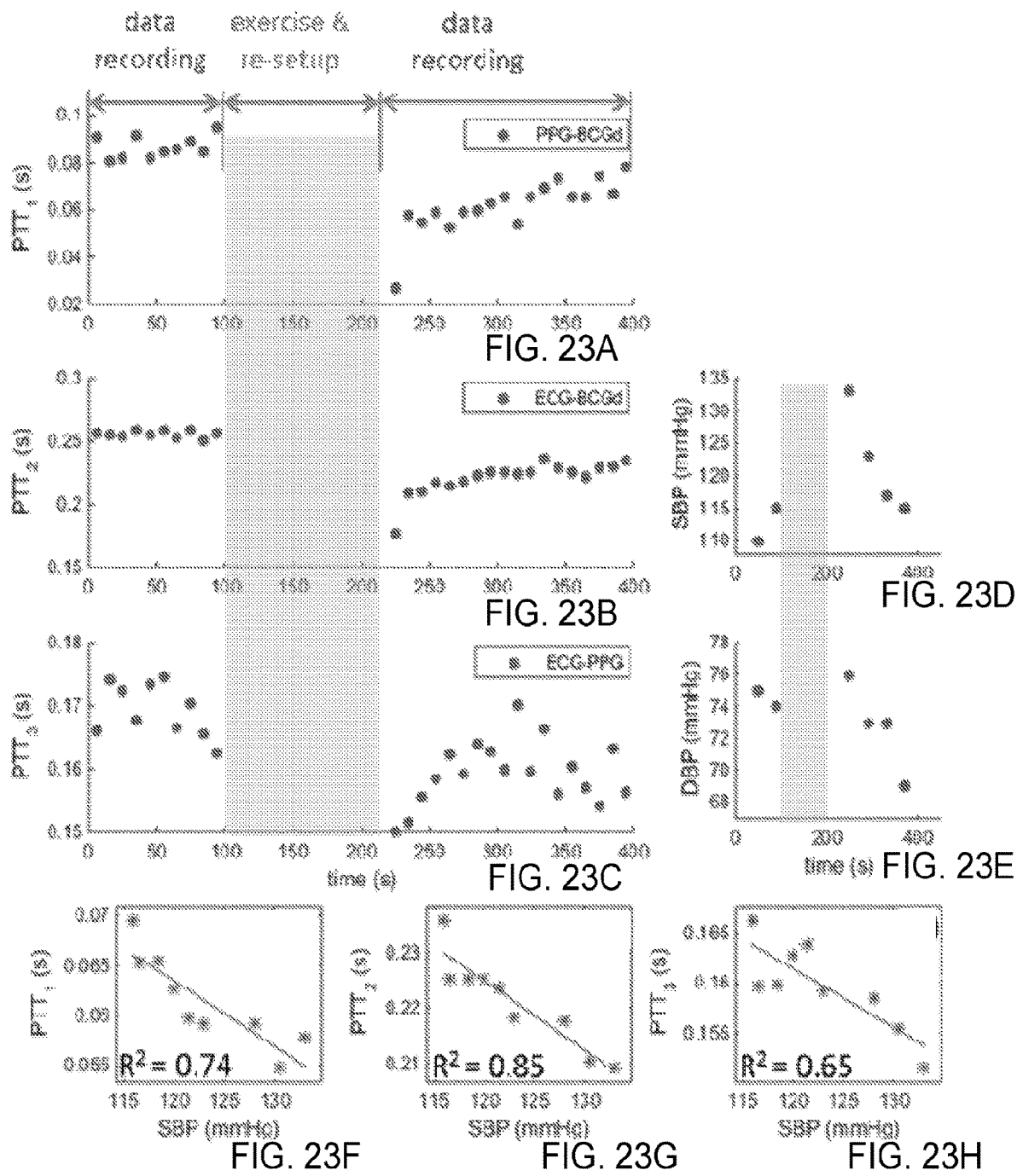
FIGS. 23A-23H are graphical representations showing PTTs and blood pressure results and correlations from subject number six, according to one aspect of the present disclosure.
Figure 24A:
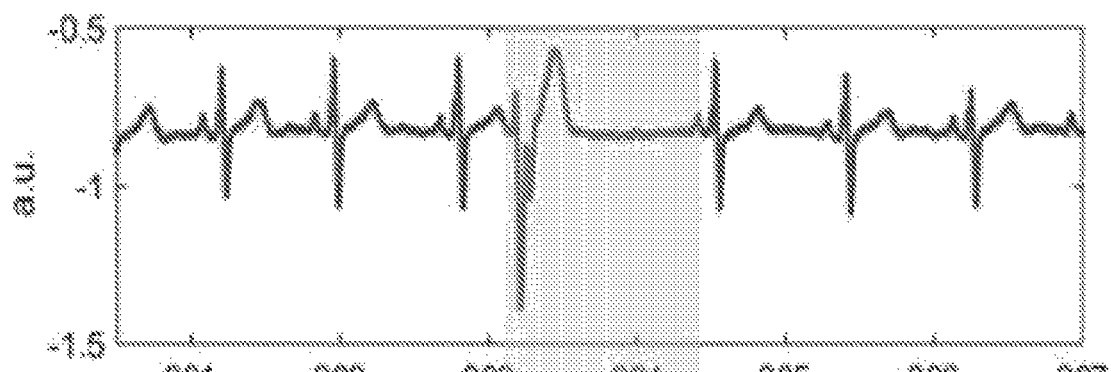
FIGS. 24A-24D are graphical representations showing PVC occurrence in different cardiac signals, according to one aspect of the present disclosure.
Figure 24B:
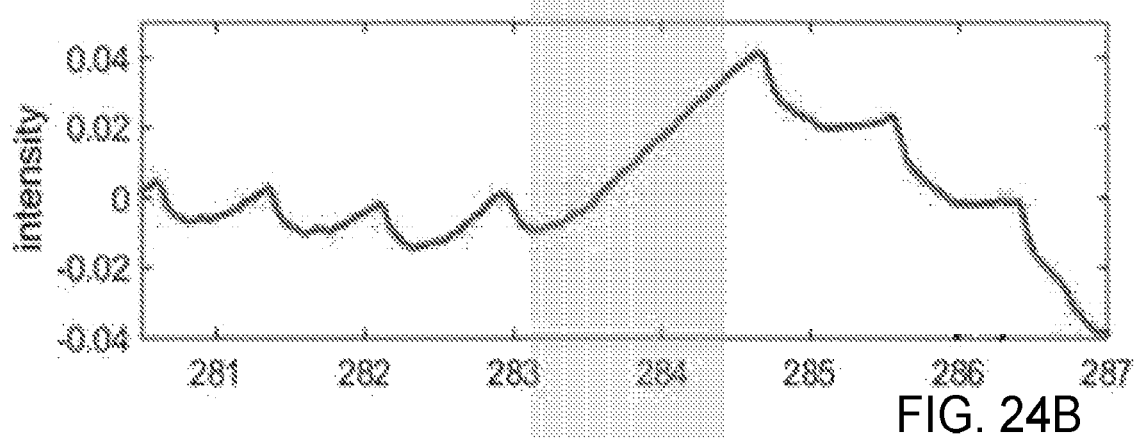
Figure 24C:
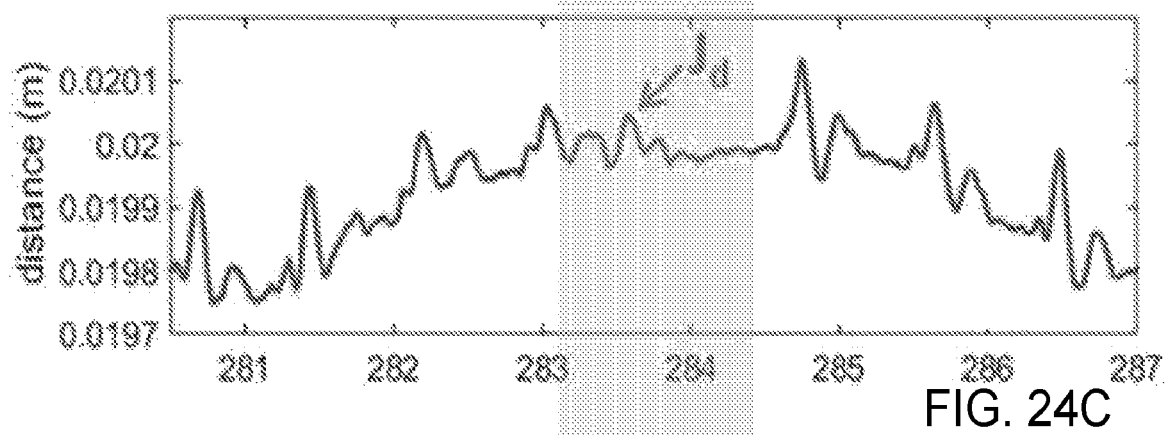
Figure 24D:
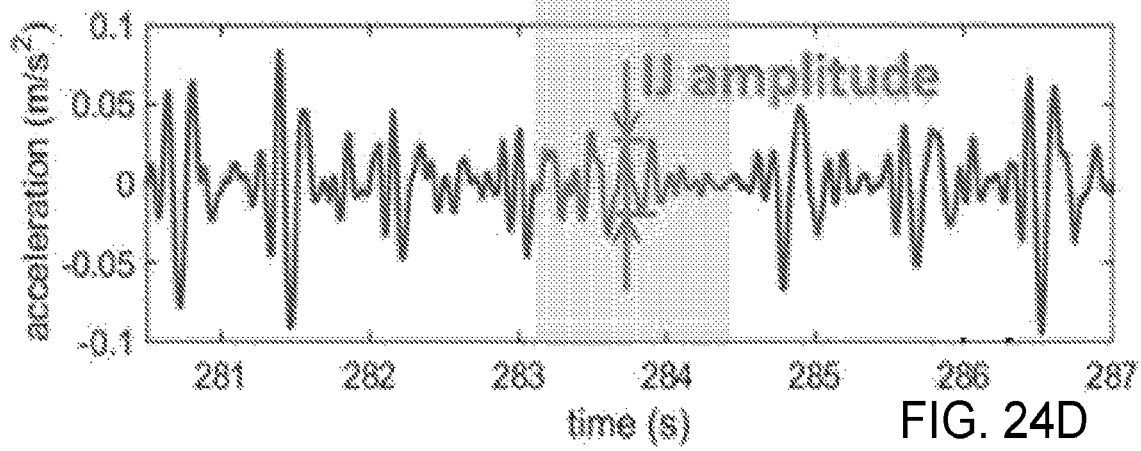
Figure 25A:
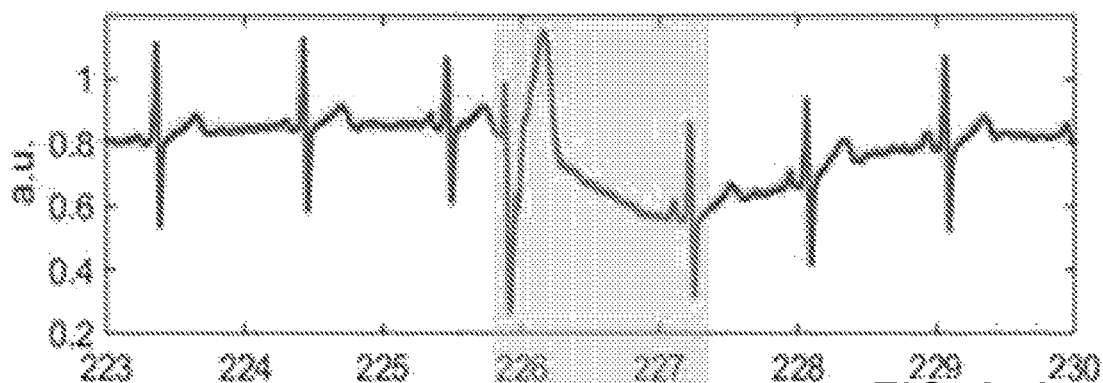
FIGS. 25A-25D are graphical representations showing PVC occurrence in the same subject on another day, according to one aspect of the present disclosure.
Figure 25B:
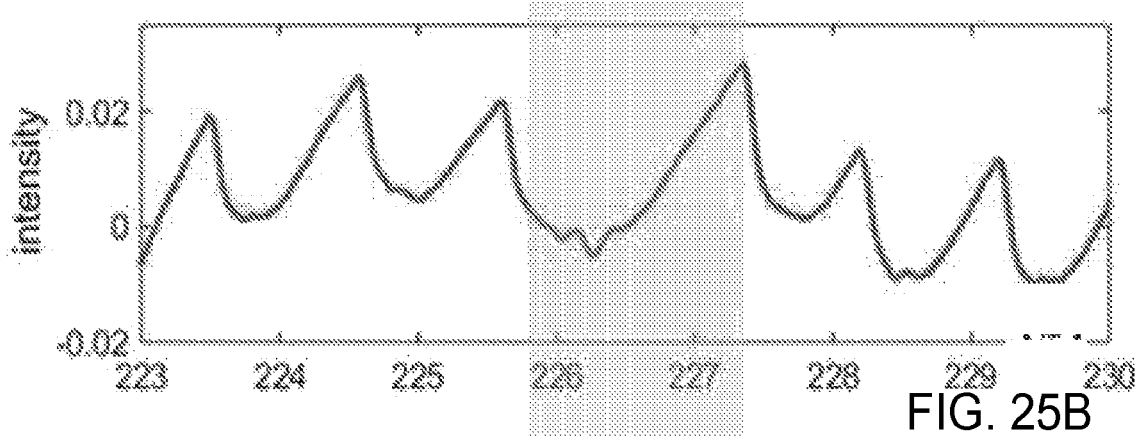
Figure 25C:
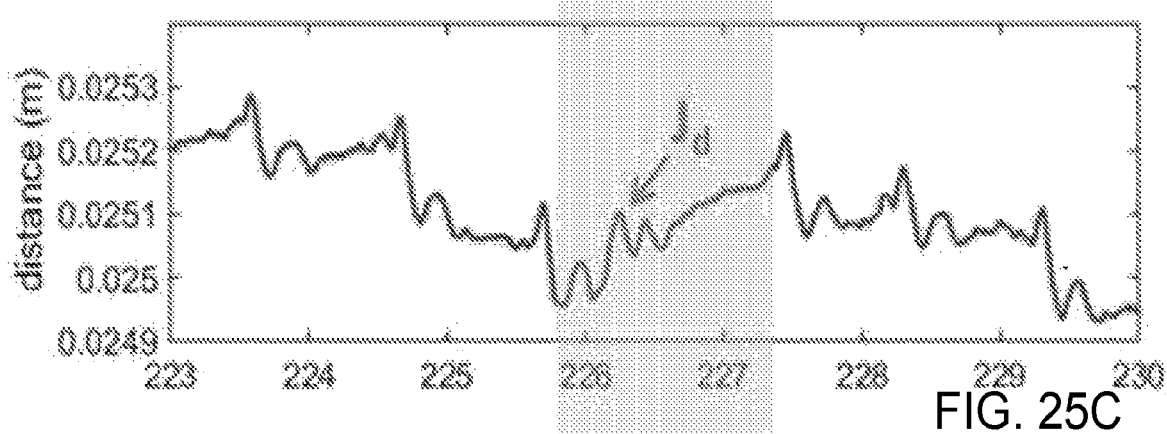
Figure 25D:
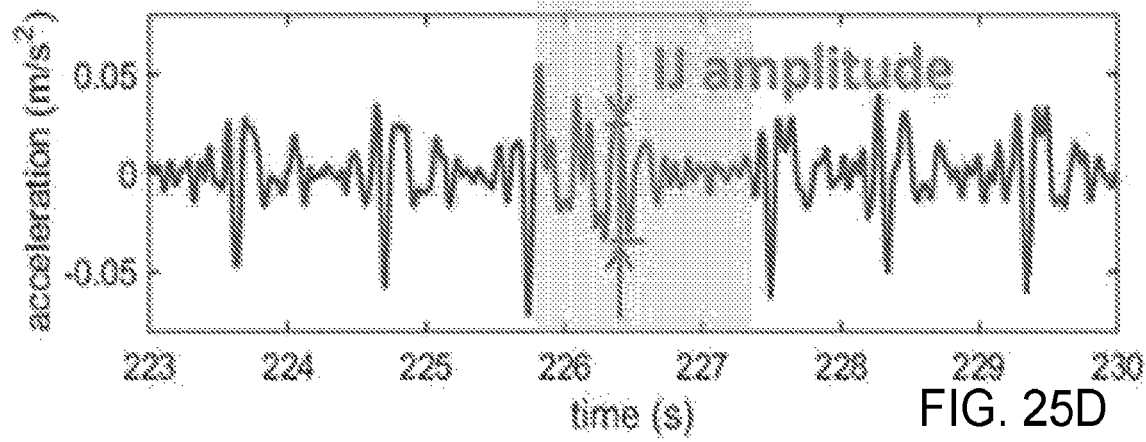

Due to the intense body motions in Stage III and IV, data recording (including video, ECG and reference BP) is not able to be performed during these two time periods. The estimated changes in BP and PTT in different stages are illustrated in FIG. 17.

FIGS. 18A-18H show the blood pressure tracking results and correlations with SBP measured by reference technology with a male subject (#1). Obtained PTT values were averaged every 10 seconds to reduce the influence of artifacts (FIGS. 18A-18C). SBP and DBP values were obtained from reference BP monitor every 50 seconds. The timing of the BP values was obtained when the BP readings were available on the display of the device. The shadow areas indicate the time periods during which measurements were not able to be obtained due to the subject having recently exercised or waiting for system setup (FIGS. 18A-18E). Correlations are calculated between PTT values and SBP during BP recovery period after exercise (FIGS. 18F-18H). The SBP values were interpolated to reach a time resolution as 10 seconds. In regular cuff-based BP device, SBP value was obtained earlier than DBP, therefore, SBP was shifted in time by 20 seconds to compensate for this delay. Outliners were removed which may have been caused by different sources of artifacts, for instance, unwanted body motions or slow response of reference method. The increase of SBP due to the subject taking exercise in the experiment was about 10 mmHg.

Correlation between blood pressure (especially SBP) and PTT values can be seen from all the plots in FIGS. 18A-18C. The trends are clearer with FIG. 18A and FIG. 18B. After taking exercise, the PTT values were lower than those before taking exercise. A quick recovery can be noticed right after the exercise and then followed by a slow climbing up. Among the three calculation methods, using PTT from PPG to BCG to track blood pressure is the main interest of my work since both PPG and BCG waveforms can be obtained by a single camera simultaneously.

FIGS. 19-23 illustrate the experimental results following the same protocols obtained from male subjects #2, #3, and female subjects #4, #5, #6.

Within all the subjects, $PTT_1$ and $PTT_2$ show overall better correlations with BP compared with $PTT_3$. Relying completely on ECG may introduce variability in the pre-ejection period, and PPG at current state has insignificant noise level. Combining these two factors together probably makes $PTT_3$ have the worst correlation with BP.

Detection of Premature Ventricular Contraction

During the experiment for BP monitoring, Premature Ventricular Contraction (PVC) was also detected with both presented video-based method and reference ECG.

PVC is the extra, abnormal heartbeat that begins in one of the heart's two lower chambers. It is a sign of decreased oxygenation to the heart muscle. It occurs in most people at some point with the feeling as "skipped beats". Causes of PVC may include medications, alcohol, anxiety and so on. For most people with isolated PVCs, treatment is not needed. However, if PVCs occur continuously for longer than 30 seconds, it may indicate serious cardiac condition.

Traditional method to diagnose PVC is based on ECG. PVC pattern can be easily distinguished from a normal heart beat. Normally, to detect PVC, the patients are required to wear a conventional Holter monitor to record ECG continuously for about 48 hours, and the data will be saved and analyzed by doctors later. The electrodes of Holter monitor are attached to the patients' chest, resulting in discomfort and limitation of freedom. Other than ECG-based methods, researchers have also reported PVC detection based on PPG and BCG waveforms with contact-based methods. In PPG recorded by sensor attached to finger, PVC can be recognized by an abnormal longer peak-peak interval. Some methods detect PVC based on acceleration BCG using weighing scale by finding the significantly lower BCG "IJ" amplitudes.

During experimentation, the occurrences of PVC were found with one subject. The frequency of PVC appearance was about twice in 5 minutes. The PVC patterns can be recognized from both PPG and BCG waveforms and the happenings of PVC were also confirmed by the synchronized ECG recordings.

FIGS. 24A-D and 25A-D show the occurrences of PVC with the same subject in different days. The shadow areas indicate the occurrences of PVC. ECG, PPG and BCG waveforms were recording simultaneously. In ECG (FIG. 24A and FIG. 25A), the abnormal forms of PVC were found in QRS-complex. In PPG (FIG. 24B and FIG. 25B), longer peak-peak intervals were found. In displacement BCG (FIG. 24C and FIG. 25C), $J_d$ peaks show lower amplitudes and the whole cycles looked uncomplete compared with regular heartbeat cycles. In acceleration BCG (FIG. 24D and FIG. 25D), the "IJ" amplitudes of PVC were lower than those in neighboring normal heartbeat cycles.

In the blood pressure experiment, the subjects were asked to take exercise to change their blood pressure. Taking exercise makes muscles need more oxygen. As a result, the heart pumps more blood around the body together with more powerful contractions which will make blood pressure increase. However, exercise may introduce extra body motions which will influence the PPG and BCG qualities, especially for BCG, which is a recording of small body movement. New test protocols may be needed to validate presented method without introduction of extra motion artifacts. One of the potential solutions is using medicine (e.g. Nitroglycerin), which will change blood pressure without extra body movements. However, the implementation of this protocol may need collaboration with professional medical staff.

Individual calibration is a limitation of blood pressure monitoring using PTT method, which is due to the individual mechanical properties of the vascular wall and other factors. Currently, PTT-based methods have been proved to track the trend of blood pressure change especially for SBP, however, getting absolute blood pressure values without calibration is difficult to achieve.

Using video-based technique potentially can provide a non-contact solution for PVC long term monitoring. A better understanding of PVC patterns in PPG and BCG may help to automatic recognition of such events.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method for monitoring an individual having a body part, the method comprising:
   receiving a set of sequential video frames of the body part of the individual at a controller, the set of sequential video frames captured using a single camera;
   defining a region of interest of the body part in a first video frame of the set of sequential video frames, the region of interest including a body feature;
   tracking motion of the body feature over the set of sequential video frames using the controller;
   generating a ballistocardiogram (BCG) waveform based on the set of sequential video frames that defines BCG signals associated with the motion of the body feature using the controller, wherein to generate the BCG waveform, the controller, for each frame of the set of sequential video frames, averages vertical components of point locations over all detected feature points of the region of interest plotted against time; and
   generating a photoplethysmogram waveform based on an image intensity averaged over the region of interest for each frame in the set of sequential video frames and plotted against time using the controller.

2. The method of claim 1, wherein the BCG waveform includes a velocity BCG waveform and an acceleration BCG waveform corresponding respectively to first and second temporal derivatives calculated from the BCG waveform.

3. The method of claim 1, further comprising: generating a pulse transit time based on a relative time shift between the BCG waveform and the photoplethysmogram waveform.

4. The method of claim 3, further comprising: determining a blood pressure for the individual from at least one of the pulse transit time, cardiac output, peripheral resistance, vessel elasticity, or blood volume.

5. The method of claim 4, further comprising:
   determining a heart rate for the individual from the BCG waveform or the photoplethysmogram waveform;
   determining a stroke volume for the individual from the BCG waveform; and
   determining the cardiac output from the heart rate and the stroke volume.

6. A system for monitoring an individual having a body part, the system comprising:
   a camera disposed relative to the body part of the individual that captures a set of sequential video frames of the body part of the individual; and
   a controller in communication with the camera, the controller adapted to generate a ballistocardiogram waveform and a photoplethysmogram waveform from the set of sequential video frames, the ballistocardiogram waveform generated from a vertical displacement of a body feature within a defined region of interest of the body part and tracked over the set of sequential video frames, the photoplethysmogram waveform generated based on an image intensity averaged over the region of interest for each frame in the set of sequential video frames and plotted against time.

7. The system of claim 6, wherein the controller generates a pulse transit time based on a relative time shift between the ballistocardiogram waveform and the photoplethysmogram waveform.

8. The system of claim 7, wherein the controller determines a blood pressure for the individual from the pulse transit time.

9. The system of claim 6, wherein the controller determines a Premature Ventricular Contraction (PVC) based on the ballistocardiogram waveform and the photoplethysmogram waveform from the set of sequential video frames.

10. The system of claim 6, wherein the ballistocardiogram waveform includes a velocity ballistocardiogram waveform and an acceleration ballistocardiogram waveform.

11. The system of claim 6, wherein the image intensity is averaged for a first color channel and a second color channel.

* * * * *